US010870871B2

(12) United States Patent
Kim et al.

(10) Patent No.: US 10,870,871 B2
(45) Date of Patent: Dec. 22, 2020

(54) POLYPEPTIDE AND METHOD FOR PRODUCING ORNITHINE-BASED PRODUCT USING THE SAME

(71) Applicant: CJ CHEILJEDANG CORPORATION, Seoul (KR)

(72) Inventors: Seon Hye Kim, Seoul (KR); Su Jin Park, Seoul (KR); Kyoung Min Lee, Seoul (KR); Kyungsu Na, Seoul (KR); Hong Xian Li, Seoul (KR); Hyun-jung Bae, Seoul (KR); Jihyun Shim, Seoul (KR); Young Lyeol Yang, Seoul (KR); Hye Won Um, Seoul (KR); Hyo Hyoung Lee, Seoul (KR); Min Gyeong Kang, Seoul (KR); Hye Won Kim, Seoul (KR); Byeong Cheol Song, Seoul (KR); Haena Oh, Seoul (KR); Han Hyoung Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/622,087

(22) PCT Filed: Jun. 14, 2018

(86) PCT No.: PCT/KR2018/006733
§ 371 (c)(1),
(2) Date: Dec. 12, 2019

(87) PCT Pub. No.: WO2018/230978
PCT Pub. Date: Dec. 20, 2018

(65) Prior Publication Data
US 2020/0181661 A1 Jun. 11, 2020

(30) Foreign Application Priority Data
Jun. 14, 2017 (KR) .................. 10-2017-0074981

(51) Int. Cl.
| | |
|---|---|
| *C12P 13/10* | (2006.01) |
| *C07K 14/00* | (2006.01) |
| *C07K 14/34* | (2006.01) |
| *C12N 1/21* | (2006.01) |
| *C12N 15/31* | (2006.01) |
| *C12N 15/77* | (2006.01) |
| *C12P 13/00* | (2006.01) |

(52) U.S. Cl.
CPC .............. *C12P 13/10* (2013.01); *C07K 14/00* (2013.01); *C12N 15/77* (2013.01); *C12P 13/001* (2013.01)

(58) Field of Classification Search
None
See application file for complete search history.

(56) References Cited

U.S. PATENT DOCUMENTS

2003/0113899 A1  6/2003  Yamaguchi et al.

FOREIGN PATENT DOCUMENTS

| | | |
|---|---|---|
| JP | 2009-254323 A | 11/2009 |
| KR | 10-0791659 B1 | 1/2008 |
| KR | 10-2012-0064045 A | 6/2012 |
| KR | 10-2013-0082478 A | 7/2013 |
| KR | 10-1372635 B1 | 3/2014 |
| KR | 10-2014-0115244 A | 9/2014 |
| KR | 10-149385 B1 | 2/2015 |
| KR | 10-1607741 B1 | 3/2016 |
| KR | 10-2017-0000906 A | 1/2017 |
| KR | 10-2017-0010960 A | 2/2017 |

OTHER PUBLICATIONS

Bellmann et al., "Expression control and specificity of the basic amino acid exporter LysE of *Corynebacterium glutamicum*," *Microbiology* 147:1765-1774, 2001.
Gotoh et al., "Direct production of L-ornithine from casein by commercial digestive enzymes and in situ activated arginase," *Bioprocess Biosyst Eng* 33:773-777, 2010 (6 pages).
Kim et al., "Metabolic Engineering of Corynebacterium glutamicum for the Production of L-Ornithine," *Biotechnology and Bioengineering* 112(2):416-421, 2015.
Matsui et al., "Detection of D-Ornithine Extracellularly Produced by *Corynebacterium glutamicum* ATCC 13032::argF," *Biosci. Biotechnol. Biochem.* 74(12):2507-2510, 2010 (5 pages).
Qian et al., "Metabolic Engineering of *Escherichia coli* for the Production of Putrescine: A Four Carbon Diamine," *Biotechnology and Bioengineering* 104(4):651-662, 2009.
Schneider et al., "Putrescine production by engineered *Corynebacterium glutamicum*," *Appl Microbiol Biotechnol* 88:859-868, 2010.

*Primary Examiner* — David Steadman
(74) *Attorney, Agent, or Firm* — Seed IP Law Group LLP

(57) ABSTRACT

The present disclosure relates to a novel polypeptide having an ability to export an ornithine-based product, and a method for producing an ornithine-based product using the same.

21 Claims, No Drawings
Specification includes a Sequence Listing.

SEQUENCE LISTING

<160> NUMBER OF SEQ ID NOS: 68

<210> SEQ ID NO 1
<211> LENGTH: 494
<212> TYPE: PRT
<213> ORGANISM: Artificial Sequence
<220> FEATURE:
<223> OTHER INFORMATION: ATCC13032 NCgl2522

<400> SEQUENCE: 1

```
Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190
```

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Ala Ala Gly Met Ala Met Phe Thr Val Ser
        275                 280                 285

Gly Leu Glu Met Thr Thr Ser Gln Arg Phe Gln Leu Ser Val Gly Phe
        290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
        370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
        450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 2
<211> LENGTH: 494
<212> TYPE: PRT
<213> ORGANISM: Artificial Sequence
<220> FEATURE:
<223> OTHER INFORMATION: ATCC13869 NCgl2522

<400> SEQUENCE: 2

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

```
Leu Met Ala Gly Leu Leu Gly Thr Gly Thr Gly Asp Lys Ile
65                  70                  75                  80

Gly His Arg Arg Met Phe Leu Met Gly Leu Ser Ile Phe Gly Ile Ala
                    85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
                115                 120                 125

Ala Leu Ile Arg Ile Thr Phe Glu Asp Glu Arg Glu Arg Asn Thr Ala
130                 135                 140

Ile Gly Ile Trp Gly Ser Val Ala Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
                195                 200                 205

Ser Ser Phe Tyr Ala Leu Leu Thr Leu Ala Gly Leu Ile Val Thr Ile
210                 215                 220

Lys Glu Ser Val Asn Thr Ala Arg His Leu Pro Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
                275                 280                 285

Gly Leu Glu Met Thr Thr Ser Gln Arg Phe Gln Leu Ser Val Gly Phe
                290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
                340                 345                 350

Leu Cys Ile Trp Gly Ala Thr His Thr Asp Gly Leu Pro Phe Phe Ile
                355                 360                 365

Ala Gly Leu Phe Phe Met Gly Ala Gly Ala Gly Ser Val Met Ser Val
                370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
                420                 425                 430

Pro Ala Glu Val Ala Asp Asn Phe Ser Ala Gly Val His His Ala Ile
                435                 440                 445

Tyr Gly Asp Ala Ala Arg Ala Ser Leu Asp Thr Ala Tyr Ile Asn Val
                450                 455                 460

Leu Ile Ile Ala Leu Val Cys Ala Val Ala Ala Leu Ile Ser Ser
465                 470                 475                 480
```

Tyr Leu Phe Arg Gly Asn Pro Lys Gly Ala Asn Asn Ala His
            485                 490

<210> SEQ ID NO 3
<211> LENGTH: 494
<212> TYPE: PRT
<213> ORGANISM: Artificial Sequence
<220> FEATURE:
<223> OTHER INFORMATION: ATCC13032 NCgl2522_M1

<400> SEQUENCE: 3

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ser Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Pro Ala Ala Thr Ala Val Gly Ile Ala
            340                 345                 350

Leu Cys Ile Trp Gly Ala Thr His Thr Asp Gly Leu Pro Phe Phe Ile
            355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
            435                 440                 445

Asp Gly Asp Ala Ala Arg Ala Ser Leu Asp Thr Ala Tyr Ile Asn Val
        450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
            485                 490

<210> SEQ ID NO 4
<211> LENGTH: 494
<212> TYPE: PRT
<213> ORGANISM: Artificial Sequence
<220> FEATURE:
<223> OTHER INFORMATION: ATCC13869 NCgl2522_M2

<400> SEQUENCE: 4

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ser Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

```
Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 5
<211> LENGTH: 494
<212> TYPE: PRT
<213> ORGANISM: Artificial Sequence
<220> FEATURE:
<223> OTHER INFORMATION: ATCC13032 NCgl2522_M3

<400> SEQUENCE: 5

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95
```

```
Ser Leu Gly Ala Ala Phe Ala Pro Thr Ala Trp Ala Leu Val Ala Ala
                100                 105                 110
Arg Ala Phe Leu Gly Ile Gly Ala Ala Thr Met Met Pro Ala Thr Leu
            115                 120                 125
Ala Leu Ile Arg Ile Thr Phe Glu Asp Glu Arg Glu Arg Asn Thr Ala
        130                 135                 140
Ile Gly Ile Trp Gly Ser Val Asn Ile Leu Gly Ala Ala Ala Gly Pro
145                 150                 155                 160
Ile Ile Gly Gly Ala Leu Leu Glu Phe Phe Trp Trp Gly Ser Val Phe
                165                 170                 175
Leu Ile Asn Val Pro Val Ala Val Ile Ala Leu Ile Ala Thr Leu Phe
            180                 185                 190
Val Ala Pro Ala Asn Ile Ala Asn Pro Ser Lys His Trp Asp Phe Leu
        195                 200                 205
Ser Ser Phe Tyr Ala Leu Leu Thr Leu Ala Gly Leu Ile Ile Thr Ile
210                 215                 220
Lys Glu Ser Val Asn Thr Ala Arg His Met Pro Leu Leu Leu Gly Ala
225                 230                 235                 240
Val Ile Met Leu Ile Ile Gly Ala Val Leu Phe Ser Ser Arg Gln Lys
                245                 250                 255
Lys Ile Glu Glu Pro Leu Leu Asp Leu Ser Leu Phe Arg Asn Arg Leu
            260                 265                 270
Phe Leu Gly Gly Val Val Ala Ala Gly Met Ala Met Phe Thr Val Ser
        275                 280                 285
Gly Leu Glu Met Thr Thr Ser Gln Arg Phe Gln Leu Ser Val Gly Phe
290                 295                 300
Thr Pro Leu Glu Ala Gly Leu Leu Met Ile Pro Ala Ala Leu Gly Ser
305                 310                 315                 320
Phe Pro Met Ser Ile Ile Gly Gly Ala Asn Leu His Arg Trp Gly Phe
                325                 330                 335
Lys Pro Leu Ile Ser Gly Gly Phe Ala Ala Thr Ala Val Gly Ile Ala
            340                 345                 350
Leu Cys Ile Trp Gly Ala Thr His Thr Asp Gly Leu Pro Phe Phe Ile
        355                 360                 365
Ala Gly Leu Phe Phe Met Gly Ala Gly Ala Gly Ser Val Met Ser Val
        370                 375                 380
Ser Ser Thr Ala Ile Ile Gly Ser Ala Pro Val Arg Lys Ala Gly Met
385                 390                 395                 400
Ala Ser Ser Ile Glu Glu Val Ser Tyr Glu Phe Gly Thr Leu Leu Ser
                405                 410                 415
Val Ala Ile Leu Gly Ser Leu Phe Pro Phe Tyr Ser Leu His Ala
            420                 425                 430
Pro Ala Glu Val Ala Asp Asn Phe Ser Ala Gly Val His His Ala Ile
        435                 440                 445
Asp Gly Asp Ala Ala Arg Ala Ser Leu Asp Thr Ala Tyr Ile Asn Val
        450                 455                 460
Leu Ile Ile Ala Leu Val Cys Ala Val Ala Ala Leu Ile Ser Ser
465                 470                 475                 480
Tyr Leu Phe Arg Gly Asn Pro Lys Gly Ala Asn Asn Ala His
                485                 490

<210> SEQ ID NO 6
<211> LENGTH: 494
<212> TYPE: PRT
```

<213> ORGANISM: Artificial Sequence
<220> FEATURE:
<223> OTHER INFORMATION: ATCC13032 NCgl2522_M4

<400> SEQUENCE: 6

```
Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
130                 135                 140

Ile Gly Ile Trp Gly Ser Val His Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Ile
        355                 360                 365

Ala Gly Leu Phe Phe Met Gly Ala Gly Ala Ser Val Met Ser Val
370                 375                 380

Ser Ser Thr Ala Ile Ile Gly Ser Ala Pro Val Arg Lys Ala Gly Met
```

```
385                 390                 395                 400
Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
                420                 425                 430

Pro Ala Glu Val Ala Asp Asn Phe Ser Ala Gly Val His His Ala Ile
                435                 440                 445

Asp Gly Asp Ala Ala Arg Ala Ser Leu Asp Thr Ala Tyr Ile Asn Val
            450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 7
<211> LENGTH: 494
<212> TYPE: PRT
<213> ORGANISM: Artificial Sequence
<220> FEATURE:
<223> OTHER INFORMATION: ATCC13032 NCgl2522_M5

<400> SEQUENCE: 7

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
                20                  25                  30

Asp Asn Ser Ile Leu Tyr Thr Ala Leu Pro Leu Leu Arg Glu Gln Leu
            35                  40                  45

Ala Ala Thr Glu Thr Gln Ala Leu Trp Ile Ile Asn Ala Tyr Pro Leu
        50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
        130                 135                 140

Ile Gly Ile Trp Gly Ser Val Pro Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Ile Thr Ile
        210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
```

-continued

```
                260                 265                 270
Phe Leu Gly Gly Val Ala Ala Gly Met Ala Met Phe Thr Val Ser
            275                 280                 285
Gly Leu Glu Met Thr Thr Ser Gln Arg Phe Gln Leu Ser Val Gly Phe
        290                 295                 300
Thr Pro Leu Glu Ala Gly Leu Leu Met Ile Pro Ala Ala Leu Gly Ser
305                 310                 315                 320
Phe Pro Met Ser Ile Ile Gly Gly Ala Asn Leu His Arg Trp Gly Phe
                325                 330                 335
Lys Pro Leu Ile Ser Gly Gly Phe Ala Ala Thr Ala Val Gly Ile Ala
            340                 345                 350
Leu Cys Ile Trp Gly Ala Thr His Thr Asp Gly Leu Pro Phe Phe Ile
        355                 360                 365
Ala Gly Leu Phe Phe Met Gly Ala Gly Ala Gly Ser Val Met Ser Val
        370                 375                 380
Ser Ser Thr Ala Ile Ile Gly Ser Ala Pro Val Arg Lys Ala Gly Met
385                 390                 395                 400
Ala Ser Ser Ile Glu Glu Val Ser Tyr Glu Phe Gly Thr Leu Leu Ser
                405                 410                 415
Val Ala Ile Leu Gly Ser Leu Phe Pro Phe Phe Tyr Ser Leu His Ala
            420                 425                 430
Pro Ala Glu Val Ala Asp Asn Phe Ser Ala Gly Val His His Ala Ile
        435                 440                 445
Asp Gly Asp Ala Ala Arg Ala Ser Leu Asp Thr Ala Tyr Ile Asn Val
    450                 455                 460
Leu Ile Ile Ala Leu Val Cys Ala Val Ala Ala Leu Ile Ser Ser
465                 470                 475                 480
Tyr Leu Phe Arg Gly Asn Pro Lys Gly Ala Asn Ala His
                485                 490

<210> SEQ ID NO 8
<211> LENGTH: 494
<212> TYPE: PRT
<213> ORGANISM: Artificial Sequence
<220> FEATURE:
<223> OTHER INFORMATION: ATCC13032 NCgl2522_M6

<400> SEQUENCE: 8

Met Thr Ser Glu Thr Leu Gln Ala Gln Ala Pro Thr Lys Thr Gln Arg
1               5                   10                  15
Trp Ala Phe Leu Ala Val Ile Ser Gly Gly Leu Phe Leu Ile Gly Val
            20                  25                  30
Asp Asn Ser Ile Leu Tyr Thr Ala Leu Pro Leu Leu Arg Glu Gln Leu
        35                  40                  45
Ala Ala Thr Glu Thr Gln Ala Leu Trp Ile Ile Asn Ala Tyr Pro Leu
    50                  55                  60
Leu Met Ala Gly Leu Leu Leu Thr Gly Thr Leu Gly Asp Lys Ile
65                  70                  75                  80
Gly His Arg Arg Met Phe Leu Met Gly Leu Ser Ile Phe Gly Ile Ala
                85                  90                  95
Ser Leu Gly Ala Ala Phe Ala Pro Thr Ala Trp Ala Leu Val Ala Ala
            100                 105                 110
Arg Ala Phe Leu Gly Ile Gly Ala Ala Thr Met Met Pro Ala Thr Leu
        115                 120                 125
Ala Leu Ile Arg Ile Thr Phe Glu Asp Glu Arg Glu Arg Asn Thr Ala
```

```
                130             135             140
Ile Gly Ile Trp Gly Ser Val Lys Ile Leu Gly Ala Ala Gly Pro
145                 150                 155                 160

Ile Ile Gly Gly Ala Leu Leu Glu Phe Phe Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Ile Thr Ile
        210                 215                 220

Lys Glu Ser Val Asn Thr Ala Arg His Met Pro Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
                275                 280                 285

Gly Leu Glu Met Thr Thr Ser Gln Arg Phe Gln Leu Ser Val Gly Phe
                290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
                340                 345                 350

Leu Cys Ile Trp Gly Ala Thr His Thr Asp Gly Leu Pro Phe Phe Ile
            355                 360                 365

Ala Gly Leu Phe Phe Met Gly Ala Gly Ala Gly Ser Val Met Ser Val
        370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
                420                 425                 430

Pro Ala Glu Val Ala Asp Asn Phe Ser Ala Gly Val His His Ala Ile
            435                 440                 445

Asp Gly Asp Ala Ala Arg Ala Ser Leu Asp Thr Ala Tyr Ile Asn Val
        450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 9
<211> LENGTH: 494
<212> TYPE: PRT
<213> ORGANISM: Artificial Sequence
<220> FEATURE:
<223> OTHER INFORMATION: ATCC13032 NCgl2522_M7

<400> SEQUENCE: 9

Met Thr Ser Glu Thr Leu Gln Ala Gln Ala Pro Thr Lys Thr Gln Arg
```

-continued

```
 1               5              10              15
Trp Ala Phe Leu Ala Val Ile Ser Gly Gly Leu Phe Leu Ile Gly Val
                 20              25              30

Asp Asn Ser Ile Leu Tyr Thr Ala Leu Pro Leu Leu Arg Glu Gln Leu
                 35              40              45

Ala Ala Thr Glu Thr Gln Ala Leu Trp Ile Ile Asn Ala Tyr Pro Leu
         50              55              60

Leu Met Ala Gly Leu Leu Leu Gly Thr Gly Thr Leu Gly Asp Lys Ile
 65              70              75              80

Gly His Arg Arg Met Phe Leu Met Gly Leu Ser Ile Phe Gly Ile Ala
                     85              90              95

Ser Leu Gly Ala Ala Phe Ala Pro Thr Ala Trp Ala Leu Val Ala Ala
                100             105             110

Arg Ala Phe Leu Gly Ile Gly Ala Ala Thr Met Met Pro Ala Thr Leu
                115             120             125

Ala Leu Ile Arg Ile Thr Phe Glu Asp Glu Arg Glu Arg Asn Thr Ala
130             135             140

Ile Gly Ile Trp Gly Ser Val Glu Ile Leu Gly Ala Ala Ala Gly Pro
145                 150             155             160

Ile Ile Gly Gly Ala Leu Leu Glu Phe Phe Trp Trp Gly Ser Val Phe
                165             170             175

Leu Ile Asn Val Pro Val Ala Val Ile Ala Leu Ile Ala Thr Leu Phe
                180             185             190

Val Ala Pro Ala Asn Ile Ala Asn Pro Ser Lys His Trp Asp Phe Leu
                195             200             205

Ser Ser Phe Tyr Ala Leu Leu Thr Leu Ala Gly Leu Ile Ile Thr Ile
    210             215             220

Lys Glu Ser Val Asn Thr Ala Arg His Met Pro Leu Leu Leu Gly Ala
225             230             235             240

Val Ile Met Leu Ile Ile Gly Ala Val Leu Phe Ser Ser Arg Gln Lys
                    245             250             255

Lys Ile Glu Glu Pro Leu Leu Asp Leu Ser Leu Phe Arg Asn Arg Leu
                260             265             270

Phe Leu Gly Gly Val Val Ala Ala Gly Met Ala Met Phe Thr Val Ser
            275             280             285

Gly Leu Glu Met Thr Thr Ser Gln Arg Phe Gln Leu Ser Val Gly Phe
        290             295             300

Thr Pro Leu Glu Ala Gly Leu Leu Met Ile Pro Ala Ala Leu Gly Ser
305             310             315             320

Phe Pro Met Ser Ile Ile Gly Gly Ala Asn Leu His Arg Trp Gly Phe
                325             330             335

Lys Pro Leu Ile Ser Gly Gly Phe Ala Ala Thr Ala Val Gly Ile Ala
                340             345             350

Leu Cys Ile Trp Gly Ala Thr His Thr Asp Gly Leu Pro Phe Phe Ile
                355             360             365

Ala Gly Leu Phe Phe Met Gly Ala Gly Ala Gly Ser Val Met Ser Val
                370             375             380

Ser Ser Thr Ala Ile Ile Gly Ser Ala Pro Val Arg Lys Ala Gly Met
385             390             395             400

Ala Ser Ser Ile Glu Glu Val Ser Tyr Glu Phe Gly Thr Leu Leu Ser
                405             410             415

Val Ala Ile Leu Gly Ser Leu Phe Pro Phe Phe Tyr Ser Leu His Ala
                420             425             430
```

```
Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 10
<211> LENGTH: 494
<212> TYPE: PRT
<213> ORGANISM: Artificial Sequence
<220> FEATURE:
<223> OTHER INFORMATION: ATCC13032 NCgl2522_M8

<400> SEQUENCE: 10

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Cys Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300
```

```
Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
            325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 11
<211> LENGTH: 494
<212> TYPE: PRT
<213> ORGANISM: Artificial Sequence
<220> FEATURE:
<223> OTHER INFORMATION: ATCC13032 NCgl2522_M9

<400> SEQUENCE: 11

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Gln Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175
```

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Ile Thr Ile
        210                 215                 220

Lys Glu Ser Val Asn Thr Ala Arg His Met Pro Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 12
<211> LENGTH: 494
<212> TYPE: PRT
<213> ORGANISM: Artificial Sequence
<220> FEATURE:
<223> OTHER INFORMATION: ATCC13032 NCgl2522_M10

<400> SEQUENCE: 12

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

```
Ala Ala Thr Glu Thr Gln Ala Leu Trp Ile Ile Asn Ala Tyr Pro Leu
    50                  55                  60

Leu Met Ala Gly Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                    85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
130                 135                 140

Ile Gly Ile Trp Gly Ser Val Met Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Ile Thr Ile
        210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
            275                 280                 285

Gly Leu Glu Met Thr Thr Ser Gln Arg Phe Gln Leu Ser Val Gly Phe
        290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460
```

```
Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490
```

<210> SEQ ID NO 13
<211> LENGTH: 494
<212> TYPE: PRT
<213> ORGANISM: Artificial Sequence
<220> FEATURE:
<223> OTHER INFORMATION: ATCC13869 NCgl2522_M11

<400> SEQUENCE: 13

```
Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
                20                  25                  30

Asp Asn Ser Ile Leu Tyr Thr Ala Leu Pro Leu Leu Arg Glu Gln Leu
            35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
    130                 135                 140

Ile Gly Ile Trp Gly Ser Val Asn Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Leu Val Gly Ala
225                 230                 235                 240

Ile Ile Leu Leu Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
            275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335
```

Lys Pro Leu Ile Ser Gly Gly Phe Leu Ala Thr Ala Val Gly Ile Ala
                340                 345                 350

Leu Cys Ile Trp Gly Ala Thr His Thr Asp Gly Leu Pro Phe Phe Ile
            355                 360                 365

Ala Gly Leu Phe Phe Met Gly Ala Gly Ala Gly Ser Val Met Ser Val
        370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 14
<211> LENGTH: 494
<212> TYPE: PRT
<213> ORGANISM: Artificial Sequence
<220> FEATURE:
<223> OTHER INFORMATION: ATCC13869 NCgl2522_M12

<400> SEQUENCE: 14

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val His Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

```
Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 15
<211> LENGTH: 494
<212> TYPE: PRT
<213> ORGANISM: Artificial Sequence
<220> FEATURE:
<223> OTHER INFORMATION: ATCC13869 NCgl2522_M13

<400> SEQUENCE: 15

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80
```

```
Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
        130                 135                 140

Ile Gly Ile Trp Gly Ser Val Pro Ile Leu Gly Ala Ala Gly Pro
145                 150                 155                 160

Ile Ile Gly Gly Ala Leu Leu Glu Phe Phe Trp Trp Gly Ser Val Phe
            165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Val Thr Ile
            210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Arg Gln Lys
            245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
            275                 280                 285

Gly Leu Glu Met Thr Thr Ser Gln Arg Phe Gln Leu Ser Val Gly Phe
            290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
            325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
            355                 360                 365

Ala Gly Leu Phe Phe Met Gly Ala Gly Ala Gly Ser Val Met Ser Val
            370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
            405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
            435                 440                 445

Tyr Gly Asp Ala Ala Arg Ala Ser Leu Asp Thr Ala Tyr Ile Asn Val
450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
            485                 490
```

<210> SEQ ID NO 16
<211> LENGTH: 494
<212> TYPE: PRT
<213> ORGANISM: Artificial Sequence
<220> FEATURE:
<223> OTHER INFORMATION: ATCC13869 NCgl2522_M14

<400> SEQUENCE: 16

```
Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
                20                  25                  30

Asp Asn Ser Ile Leu Tyr Thr Ala Leu Pro Leu Leu Arg Glu Gln Leu
            35                  40                  45

Ala Ala Thr Glu Thr Gln Ala Leu Trp Ile Ile Asn Ala Tyr Pro Leu
        50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
        130                 135                 140

Ile Gly Ile Trp Gly Ser Val Lys Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
            195                 200                 205

Ser Ser Phe Tyr Ala Leu Leu Thr Leu Ala Gly Leu Ile Val Thr Ile
        210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
```

```
                    370                 375                 380
Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
            435                 440                 445

Tyr Gly Asp Ala Ala Arg Ala Ser Leu Asp Thr Ala Tyr Ile Asn Val
        450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 17
<211> LENGTH: 494
<212> TYPE: PRT
<213> ORGANISM: Artificial Sequence
<220> FEATURE:
<223> OTHER INFORMATION: ATCC13869 NCgl2522_M15

<400> SEQUENCE: 17

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Glu Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
```

Lys Ile Glu Glu Pro Leu Leu Asp Leu Ser Leu Phe Arg Asn Arg Leu
                245                 250                 255
Phe Leu Gly Gly Val Val Ala Ala Gly Met Ala Met Phe Thr Val Ser
            260                 265                 270
Gly Leu Glu Met Thr Thr Ser Gln Arg Phe Gln Leu Ser Val Gly Phe
        275                 280                 285
Thr Pro Leu Glu Ala Gly Leu Leu Met Ile Pro Ala Ala Leu Gly Ser
290                 295                 300
Phe Pro Met Ser Ile Ile Gly Gly Ala Asn Leu His Arg Trp Gly Phe
305                 310                 315                 320
Lys Pro Leu Ile Ser Gly Gly Phe Leu Ala Thr Ala Val Gly Ile Ala
            325                 330                 335
Leu Cys Ile Trp Gly Ala Thr His Thr Asp Gly Leu Pro Phe Phe Ile
        340                 345                 350
Ala Gly Leu Phe Phe Met Gly Ala Gly Ala Ser Val Met Ser Val
    355                 360                 365
Ser Ser Thr Ala Ile Ile Gly Ser Ala Pro Val Arg Lys Ala Gly Met
370                 375                 380
Ala Ser Ser Ile Glu Glu Val Ser Tyr Glu Phe Gly Thr Leu Leu Ser
385                 390                 395                 400
Val Ala Ile Leu Gly Ser Leu Phe Pro Phe Phe Tyr Ser Leu His Ala
            405                 410                 415
Pro Ala Glu Val Ala Asp Asn Phe Ser Ala Gly Val His His Ala Ile
        420                 425                 430
Tyr Gly Asp Ala Ala Arg Ala Ser Leu Asp Thr Ala Tyr Ile Asn Val
    435                 440                 445
Leu Ile Ile Ala Leu Val Cys Ala Val Ala Ala Leu Ile Ser Ser
450                 455                 460
Tyr Leu Phe Arg Gly Asn Pro Lys Gly Ala Asn Asn Ala His
465                 470                 475                 480

485                 490

<210> SEQ ID NO 18
<211> LENGTH: 494
<212> TYPE: PRT
<213> ORGANISM: Artificial Sequence
<220> FEATURE:
<223> OTHER INFORMATION: ATCC13869 NCgl2522_M16

<400> SEQUENCE: 18

Met Ile Ser Glu Thr Leu Gln Ala Gln Ala Pro Thr Lys Thr Gln Arg
1               5                   10                  15
Trp Ala Phe Leu Ala Val Ile Ser Gly Gly Leu Phe Leu Ile Gly Val
            20                  25                  30
Asp Asn Ser Ile Leu Tyr Thr Ala Leu Pro Leu Leu Arg Glu Gln Leu
        35                  40                  45
Ala Ala Thr Glu Thr Gln Ala Leu Trp Ile Ile Asn Ala Tyr Pro Leu
    50                  55                  60
Leu Met Ala Gly Leu Leu Leu Gly Thr Gly Thr Leu Gly Asp Lys Ile
65                  70                  75                  80
Gly His Arg Arg Met Phe Leu Met Gly Leu Ser Ile Phe Gly Ile Ala
                85                  90                  95
Ser Leu Gly Ala Ala Phe Ala Pro Thr Ala Trp Ala Leu Val Ala Ala
            100                 105                 110
Arg Ala Phe Leu Gly Ile Gly Ala Ala Thr Met Met Pro Ala Thr Leu 115                 120                 125
Ala Leu Ile Arg Ile Thr Phe Glu Asp Glu Arg Glu Arg Asn Thr Ala
            130                 135                 140

Ile Gly Ile Trp Gly Ser Val Cys Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
        210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
        290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
        370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
        450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 19
<211> LENGTH: 494
<212> TYPE: PRT
<213> ORGANISM: Artificial Sequence
<220> FEATURE:
<223> OTHER INFORMATION: ATCC13869 NCgl2522_M17

<400> SEQUENCE: 19

```
Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Gln Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415
```

-continued

```
Val Ala Ile Leu Gly Ser Leu Phe Pro Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 20
<211> LENGTH: 494
<212> TYPE: PRT
<213> ORGANISM: Artificial Sequence
<220> FEATURE:
<223> OTHER INFORMATION: ATCC13869 NCgl2522_M18

<400> SEQUENCE: 20

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Met Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285
```

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Ala Asn Leu His Arg Trp Gly Phe
                325                 330                 335

Lys Pro Leu Ile Ser Gly Gly Phe Leu Ala Thr Ala Val Gly Ile Ala
                340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
                420                 425                 430

Pro Ala Glu Val Ala Asp Asn Phe Ser Ala Gly Val His His Ala Ile
            435                 440                 445

Tyr Gly Asp Ala Ala Arg Ala Ser Leu Asp Thr Ala Tyr Ile Asn Val
450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
            485                 490

<210> SEQ ID NO 21
<211> LENGTH: 36
<212> TYPE: DNA
<213> ORGANISM: Artificial Sequence
<220> FEATURE:
<223> OTHER INFORMATION: Primer 13032-putE-EF-FX

<400> SEQUENCE: 21
ccggggatcc tctagaactt cagaaacctt acaggc                     36

<210> SEQ ID NO 22
<211> LENGTH: 36
<212> TYPE: DNA
<213> ORGANISM: Artificial Sequence
<220> FEATURE:
<223> OTHER INFORMATION: Primer 13032-putE-EF-RX

<400> SEQUENCE: 22
gcaggtcgac tctagactag tgcgcattat tggctc                     36

<210> SEQ ID NO 23
<211> LENGTH: 27
<212> TYPE: DNA
<213> ORGANISM: Artificial Sequence
<220> FEATURE:
<223> OTHER INFORMATION: Primer SM_putE_A152-F
<220> FEATURE:
<221> NAME/KEY: misc_feature
<222> LOCATION: (1)...(27)
<223> OTHER INFORMATION: n = A,T,C or G

<400> SEQUENCE: 23
tggggttccg tgnnkattct tggcgct                               27

<210> SEQ ID NO 24
<211> LENGTH: 27
<212> TYPE: DNA
<213> ORGANISM: Artificial Sequence
<220> FEATURE:
<223> OTHER INFORMATION: Primer SM_putE_A152-R
<220> FEATURE:
<221> NAME/KEY: misc_feature
<222> LOCATION: (1)...(27)
<223> OTHER INFORMATION: n = A,T,C or G

<400> SEQUENCE: 24
agcgccaaga atmnncacgg aacccca                                              27

<210> SEQ ID NO 25
<211> LENGTH: 34
<212> TYPE: DNA
<213> ORGANISM: Artificial Sequence
<220> FEATURE:
<223> OTHER INFORMATION: Primer pDC-putE-up-FX

<400> SEQUENCE: 25
ccggggatcc tctagagtgg tctctttctg atcg                                      34

<210> SEQ ID NO 26
<211> LENGTH: 34
<212> TYPE: DNA
<213> ORGANISM: Artificial Sequence
<220> FEATURE:
<223> OTHER INFORMATION: Primer pDC-putE-down-RX

<400> SEQUENCE: 26
gcaggtcgac tctagagcaa ttccttgtcc cagt                                      34

<210> SEQ ID NO 27
<211> LENGTH: 23
<212> TYPE: DNA
<213> ORGANISM: Artificial Sequence
<220> FEATURE:
<223> OTHER INFORMATION: Primer 13032-putE-A152S-F

<400> SEQUENCE: 27
gggttccgtg tccattcttg gcg                                                  23

<210> SEQ ID NO 28
<211> LENGTH: 23
<212> TYPE: DNA
<213> ORGANISM: Artificial Sequence
<220> FEATURE:
<223> OTHER INFORMATION: Primer 13032-putE-A152S-R

<400> SEQUENCE: 28
cgccaagaat ggacacggaa ccc                                                  23

<210> SEQ ID NO 29
<211> LENGTH: 23
<212> TYPE: DNA
<213> ORGANISM: Artificial Sequence
<220> FEATURE:
<223> OTHER INFORMATION: Primer 13032-putE-A152N-F

<400> SEQUENCE: 29
gggttccgtg aatattcttg gcg                                                  23

<210> SEQ ID NO 30

<210> SEQ ID NO 30
<211> LENGTH: 23
<212> TYPE: DNA
<213> ORGANISM: Artificial Sequence
<220> FEATURE:
<223> OTHER INFORMATION: Primer 13032-putE-A152N-R

<400> SEQUENCE: 30
cgccaagaat attcacggaa ccc                                        23

<210> SEQ ID NO 31
<211> LENGTH: 23
<212> TYPE: DNA
<213> ORGANISM: Artificial Sequence
<220> FEATURE:
<223> OTHER INFORMATION: Primer 13032-putE-A152H-F

<400> SEQUENCE: 31
gggttccgtg catattcttg gcg                                        23

<210> SEQ ID NO 32
<211> LENGTH: 23
<212> TYPE: DNA
<213> ORGANISM: Artificial Sequence
<220> FEATURE:
<223> OTHER INFORMATION: Primer 13032-putE-A152H-R

<400> SEQUENCE: 32
cgccaagaat atgcacggaa ccc                                        23

<210> SEQ ID NO 33
<211> LENGTH: 23
<212> TYPE: DNA
<213> ORGANISM: Artificial Sequence
<220> FEATURE:
<223> OTHER INFORMATION: Primer 13032-putE-A152P-F

<400> SEQUENCE: 33
gggttccgtg cctattcttg gcg                                        23

<210> SEQ ID NO 34
<211> LENGTH: 23
<212> TYPE: DNA
<213> ORGANISM: Artificial Sequence
<220> FEATURE:
<223> OTHER INFORMATION: Primer 13032-putE-A152P-R

<400> SEQUENCE: 34
cgccaagaat aggcacggaa ccc                                        23

<210> SEQ ID NO 35
<211> LENGTH: 23
<212> TYPE: DNA
<213> ORGANISM: Artificial Sequence
<220> FEATURE:
<223> OTHER INFORMATION: Primer 13032-putE-A152K-F

<400> SEQUENCE: 35
gggttccgtg aagattcttg gcg                                        23

<210> SEQ ID NO 36
<211> LENGTH: 23
<212> TYPE: DNA
<213> ORGANISM: Artificial Sequence
<220> FEATURE:
<223> OTHER INFORMATION: Primer 13032-putE-A152K-R

<400> SEQUENCE: 36
cgccaagaat cttcacggaa ccc                                              23

<210> SEQ ID NO 37
<211> LENGTH: 23
<212> TYPE: DNA
<213> ORGANISM: Artificial Sequence
<220> FEATURE:
<223> OTHER INFORMATION: Primer 13032-putE-A152E-F

<400> SEQUENCE: 37
gggttccgtg gagattcttg gcg                                              23

<210> SEQ ID NO 38
<211> LENGTH: 23
<212> TYPE: DNA
<213> ORGANISM: Artificial Sequence
<220> FEATURE:
<223> OTHER INFORMATION: Primer 13032-putE-A152E-R

<400> SEQUENCE: 38
cgccaagaat ctccacggaa ccc                                              23

<210> SEQ ID NO 39
<211> LENGTH: 23
<212> TYPE: DNA
<213> ORGANISM: Artificial Sequence
<220> FEATURE:
<223> OTHER INFORMATION: Primer 13032-putE-A152C-F

<400> SEQUENCE: 39
gggttccgtg tgtattcttg gcg                                              23

<210> SEQ ID NO 40
<211> LENGTH: 23
<212> TYPE: DNA
<213> ORGANISM: Artificial Sequence
<220> FEATURE:
<223> OTHER INFORMATION: Primer 13032-putE-A152C-R

<400> SEQUENCE: 40
cgccaagaat acacacggaa ccc                                              23

<210> SEQ ID NO 41
<211> LENGTH: 23
<212> TYPE: DNA
<213> ORGANISM: Artificial Sequence
<220> FEATURE:
<223> OTHER INFORMATION: Primer 13032-putE-A152Q-F

<400> SEQUENCE: 41
gggttccgtg cagattcttg gcg                                              23

<210> SEQ ID NO 42
<211> LENGTH: 23
<212> TYPE: DNA
<213> ORGANISM: Artificial Sequence
<220> FEATURE:
<223> OTHER INFORMATION: Primer 13032-putE-A152Q-R

<400> SEQUENCE: 42
cgccaagaat ctgcacggaa ccc                                              23

<210> SEQ ID NO 43
<211> LENGTH: 23
<212> TYPE: DNA

```
<213> ORGANISM: Artificial Sequence
<220> FEATURE:
<223> OTHER INFORMATION: Primer 13032-putE-A152M-F

<400> SEQUENCE: 43
gggttccgtg atgattcttg gcg                                               23

<210> SEQ ID NO 44
<211> LENGTH: 23
<212> TYPE: DNA
<213> ORGANISM: Artificial Sequence
<220> FEATURE:
<223> OTHER INFORMATION: Primer 13032-putE-A152M-R

<400> SEQUENCE: 44
cgccaagaat catcacggaa ccc                                               23

<210> SEQ ID NO 45
<211> LENGTH: 23
<212> TYPE: DNA
<213> ORGANISM: Artificial Sequence
<220> FEATURE:
<223> OTHER INFORMATION: Primer 13869-putE-A152S-F

<400> SEQUENCE: 45
gggttctgtg tccattcttg gcg                                               23

<210> SEQ ID NO 46
<211> LENGTH: 23
<212> TYPE: DNA
<213> ORGANISM: Artificial Sequence
<220> FEATURE:
<223> OTHER INFORMATION: Primer 13869-putE-A152S-R

<400> SEQUENCE: 46
cgccaagaat ggacacagaa ccc                                               23

<210> SEQ ID NO 47
<211> LENGTH: 23
<212> TYPE: DNA
<213> ORGANISM: Artificial Sequence
<220> FEATURE:
<223> OTHER INFORMATION: Primer 13869-putE-A152N-F

<400> SEQUENCE: 47
gggttctgtg aatattcttg gcg                                               23

<210> SEQ ID NO 48
<211> LENGTH: 23
<212> TYPE: DNA
<213> ORGANISM: Artificial Sequence
<220> FEATURE:
<223> OTHER INFORMATION: Primer 13869-putE-A152N-R

<400> SEQUENCE: 48
cgccaagaat attcacagaa ccc                                               23

<210> SEQ ID NO 49
<211> LENGTH: 23
<212> TYPE: DNA
<213> ORGANISM: Artificial Sequence
<220> FEATURE:
<223> OTHER INFORMATION: Primer 13869-putE-A152H-F

<400> SEQUENCE: 49
gggttctgtg catattcttg gcg                                               23
```

<210> SEQ ID NO 50
<211> LENGTH: 23
<212> TYPE: DNA
<213> ORGANISM: Artificial Sequence
<220> FEATURE:
<223> OTHER INFORMATION: Primer 13869-putE-A152H-R

<400> SEQUENCE: 50
cgccaagaat atgcacagaa ccc        23

<210> SEQ ID NO 51
<211> LENGTH: 23
<212> TYPE: DNA
<213> ORGANISM: Artificial Sequence
<220> FEATURE:
<223> OTHER INFORMATION: Primer 13869-putE-A152P-F

<400> SEQUENCE: 51
gggttctgtg cctattcttg gcg        23

<210> SEQ ID NO 52
<211> LENGTH: 23
<212> TYPE: DNA
<213> ORGANISM: Artificial Sequence
<220> FEATURE:
<223> OTHER INFORMATION: Primer 13869-putE-A152P-R

<400> SEQUENCE: 52
cgccaagaat aggcacagaa ccc        23

<210> SEQ ID NO 53
<211> LENGTH: 23
<212> TYPE: DNA
<213> ORGANISM: Artificial Sequence
<220> FEATURE:
<223> OTHER INFORMATION: Primer 13869-putE-A152K-F

<400> SEQUENCE: 53
gggttctgtg aagattcttg gcg        23

<210> SEQ ID NO 54
<211> LENGTH: 23
<212> TYPE: DNA
<213> ORGANISM: Artificial Sequence
<220> FEATURE:
<223> OTHER INFORMATION: Primer 13869-putE-A152K-R

<400> SEQUENCE: 54
cgccaagaat cttcacagaa ccc        23

<210> SEQ ID NO 55
<211> LENGTH: 23
<212> TYPE: DNA
<213> ORGANISM: Artificial Sequence
<220> FEATURE:
<223> OTHER INFORMATION: Primer 13869-putE-A152E-F

<400> SEQUENCE: 55
gggttctgtg gagattcttg gcg        23

<210> SEQ ID NO 56
<211> LENGTH: 23
<212> TYPE: DNA
<213> ORGANISM: Artificial Sequence
<220> FEATURE:

<223> OTHER INFORMATION: Primer 13869-putE-A152E-R

<400> SEQUENCE: 56
cgccaagaat ctccacagaa ccc					23

<210> SEQ ID NO 57
<211> LENGTH: 23
<212> TYPE: DNA
<213> ORGANISM: Artificial Sequence
<220> FEATURE:
<223> OTHER INFORMATION: Primer 13869-putE-A152C-F

<400> SEQUENCE: 57
gggttctgtg tgtattcttg gcg					23

<210> SEQ ID NO 58
<211> LENGTH: 23
<212> TYPE: DNA
<213> ORGANISM: Artificial Sequence
<220> FEATURE:
<223> OTHER INFORMATION: Primer 13869-putE-A152C-R

<400> SEQUENCE: 58
cgccaagaat acacacagaa ccc					23

<210> SEQ ID NO 59
<211> LENGTH: 23
<212> TYPE: DNA
<213> ORGANISM: Artificial Sequence
<220> FEATURE:
<223> OTHER INFORMATION: Primer 13869-putE-A152Q-F

<400> SEQUENCE: 59
gggttctgtg cagattcttg gcg					23

<210> SEQ ID NO 60
<211> LENGTH: 23
<212> TYPE: DNA
<213> ORGANISM: Artificial Sequence
<220> FEATURE:
<223> OTHER INFORMATION: Primer 13869-putE-A152Q-R

<400> SEQUENCE: 60
cgccaagaat ctgcacagaa ccc					23

<210> SEQ ID NO 61
<211> LENGTH: 23
<212> TYPE: DNA
<213> ORGANISM: Artificial Sequence
<220> FEATURE:
<223> OTHER INFORMATION: Primer 13869-putE-A152M-F

<400> SEQUENCE: 61
gggttctgtg atgattcttg gcg					23

<210> SEQ ID NO 62
<211> LENGTH: 23
<212> TYPE: DNA
<213> ORGANISM: Artificial Sequence
<220> FEATURE:
<223> OTHER INFORMATION: Primer 13869-putE-A152M-R

<400> SEQUENCE: 62
cgccaagaat catcacagaa ccc					23

```
<210> SEQ ID NO 63
<211> LENGTH: 37
<212> TYPE: DNA
<213> ORGANISM: Artificial Sequence
<220> FEATURE:
<223> OTHER INFORMATION: Primer NCgl2522-L5

<400> SEQUENCE: 63
tgcaggtcga ctctagagtt ctgcgtagct gtgtgcc                              37

<210> SEQ ID NO 64
<211> LENGTH: 31
<212> TYPE: DNA
<213> ORGANISM: Artificial Sequence
<220> FEATURE:
<223> OTHER INFORMATION: Primer NCgl2522-L3

<400> SEQUENCE: 64
gatgtttctg gatcgtaact gtaacgaatg g                                    31

<210> SEQ ID NO 65
<211> LENGTH: 24
<212> TYPE: DNA
<213> ORGANISM: Artificial Sequence
<220> FEATURE:
<223> OTHER INFORMATION: Primer CJ7-F

<400> SEQUENCE: 65
agaaacatcc cagcgctact aata                                            24

<210> SEQ ID NO 66
<211> LENGTH: 23
<212> TYPE: DNA
<213> ORGANISM: Artificial Sequence
<220> FEATURE:
<223> OTHER INFORMATION: Primer CJ7-R

<400> SEQUENCE: 66
agtgtttcct ttcgttgggt acg                                             23

<210> SEQ ID NO 67
<211> LENGTH: 41
<212> TYPE: DNA
<213> ORGANISM: Artificial Sequence
<220> FEATURE:
<223> OTHER INFORMATION: Primer NCgl2522-R5

<400> SEQUENCE: 67
caacgaaagg aaacactatg atttcagaaa ctttgcaggc g                         41

<210> SEQ ID NO 68
<211> LENGTH: 40
<212> TYPE: DNA
<213> ORGANISM: Artificial Sequence
<220> FEATURE:
<223> OTHER INFORMATION: Primer NCgl2522-R3

<400> SEQUENCE: 68
tcggtacccg gggatcccac aaaaagcgta gcgatcaacg                           40
```

POLYPEPTIDE AND METHOD FOR PRODUCING ORNITHINE-BASED PRODUCT USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_459USPC_SEQUENCE_LISTING.txt. The text file is 85 KB, was created on Dec. 10, 2019, and is being submitted electronically via EFS-Web.

TECHNICAL FIELD

The present disclosure relates to a novel polypeptide having an ability to export an ornithine-based product, and a method for producing an ornithine-based product using the same.

BACKGROUND ART

Ornithine, which is a material widely found in plants, animals, and microorganisms, is biosynthesized from glutamate, and is used as a precursor in the biosynthesis of putrescine, citrulline, and proline. Further, ornithine plays an important role in the pathway for excretion of urea produced from amino acids or ammonia by the ornithine cycle in the in vivo metabolism of higher animals. Ornithine is effective in enhancing muscle growth and reducing body fat and thus is used as nutrient supplements and also as pharmaceutical drugs for improving liver cirrhosis and liver function disorders. The known methods for producing ornithine include treatment of milk casein with digestive enzymes and use of transformed *E. coli* or a microorganism of the genus *Corynebacterium* (Korean Patent No. 10-1372635; T. Gotoh et al., *Bioprocess Biosyst. Eng.*, 33: 773-777, 2010).

Putrescine (or 1,4-butanediamine) is a very important raw material for the production of polyamide-4, 6 including nylon-4, 6, and can be produced on an industrial scale by hydrogenation of succinonitrile, which is produced from acrylonitrile by addition of hydrogen cyanide. The synthesis pathway of these chemical substances requires non-renewable petrochemical products as raw materials. Additionally, high temperature and pressure, which are implicated with the use of expensive catalyst systems, as well as relatively complex preparation steps and equipment are also needed. Accordingly, as an alternative to the chemical production process, a process of producing putrescine from a renewable biomass-derived carbon source is required. Recently, studies have been continuously conducted to use environment-friendly microorganisms for the production of industrially available high-concentration polyamines (putrescine) (Qian Z G, et al., *Biotechnol Bioeng*, 104: 651-662, 2009; Schneider J, et al., *Appl Microbiol Biotechnol*, 88: 859-868, 2010).

Meanwhile, NCgl2522 has been identified as a gene having an ability to export putrescine (Korean Patent No. 2014-0115244). However, in order to produce putrescine in a higher yield, there is still a need to develop a protein with an improved ability to export putrescine which can more effectively export putrescine from a putrescine-producing strain.

L-arginine has been widely used in medicines as hepatic function-promoting agents, brain function-promoting agents, and as ingredients of multiple amino acid supplements. Additionally, L-arginine has gained much interest in food industry as a food additive for fish cakes and health beverages, and as a salt substitute for hypertension patients. Studies have been continuously conducted to use microorganisms for the production of industrially available high-concentration arginine, and examples thereof include a method of using a mutant strain induced from the microorganism belonging to the genus *Brevibacterium* or *Corynebacterium*, which is a glutamate-producing strain, or a method of using an amino acid-producing strain, whose growth is improved through cell fusion. Meanwhile, lysE of the microorganism belonging to the genus *Corynebacterium* having an ability to export L-lysine has also been shown to export the same basic amino acid L-arginine (Bellmann A, et al, *Microbiology*, 147:1765-1774, 2001). Further, a method for enhancing the production ability of L-arginine-producing strains through the enhancement of the gene above has been known (U.S. Patent No. 2002-196232).

DISCLOSURE

Technical Problem

The present inventors have made extensive efforts to develop a variant of an export protein capable of further improving the production ability by enhancing the ability to export an ornithine product, and as a result, it was confirmed that the ability to export an ornithine-based product was enhanced when a modification was introduced on a specific site of the amino acid sequence of the NCgl2522 protein. Accordingly, they have found that putrescine or arginine, which is an ornithine-based product, can be produced in high yield by introducing the protein variant into putrescine- or arginine-producing strains, thereby completing the present invention.

Technical Solution

One object of the present disclosure is to provide a novel polypeptide having an ability to export an ornithine-based product.

Another object of the present disclosure is to provide a polynucleotide encoding the polypeptide, and a vector comprising the polynucleotide.

Still another object of the present disclosure is to provide a microorganism producing an ornithine-based product, comprising the polypeptide or having an enhanced activity thereof.

Still another object of the present disclosure is to provide a method for producing an ornithine-based product, comprising:

(i) culturing the microorganism of the genus *Corynebacterium* producing an ornithine-based product in a medium; and (ii) recovering an ornithine-based product from the microorganism or the medium obtained above.

Advantageous Effects

The polypeptide having an ability to export an ornithine-based product of the present disclosure shows an excellent activity for exporting an ornithine-based product and thus, the ability to produce an ornithine-based product can be further improved when such an activity is introduced into a microorganism producing an ornithine-based product.

DETAILED DESCRIPTION OF PREFERRED EMBODIMENTS

The present disclosure will be described in detail as follows. Meanwhile, the explanations and embodiments disclosed in the present disclosure may be applied to other explanations and embodiments, respectively. That is, all combinations of various elements disclosed herein belong to the scope of the present disclosure. Additionally, the scope of the present disclosure should not be limited by the specific descriptions described hereinbelow.

In order to achieve the objects above, an aspect of the present disclosure provides a novel polypeptide having an ability to export an ornithine-based product, wherein the alanine residue at position 152 from the N-terminus of the amino acid sequence of an ornithine-based product-exporting protein is substituted with other amino acids.

As used herein, the ornithine-based product-exporting protein refers to a protein which plays a role in the extracellular export of the products biosynthesized from ornithine as a precursor, and specifically refers to a protein which plays a role in the extracellular export of putrescine or arginine. More specifically, it may be NCgl2522 protein disclosed in Korean Patent Application Publication No. 2014-0115244. The NCgl2522 protein may, for example, consist of an amino acid sequence of SEQ ID NO: 1 or SEQ ID NO: 2, but any sequence having the activity identical to the protein may be included without limitation, and the sequence information thereof can be obtained from GenBank of NCBI, a known database.

The novel polypeptide having an ability to export an ornithine-based product of the present disclosure has a feature in which the alanine residue at position 152 from the N-terminus of the amino acid sequence of a putrescine-exporting protein is substituted with other amino acids, and thus has an improved ability to export an ornithine-based product as compared to a non-modified polypeptide, specifically, a polypeptide having an alanine residue at position 152. The other amino acids may include serine, asparagine, histidine, proline, lysine, glutamic acid, cysteine, glutamine, or methionine, but are not limited thereto. Therefore, the polypeptide having an ability to export an ornithine-based product may be, for example, those in which the alanine at position 152 in the amino acid sequence of an ornithine-based product-exporting protein is substituted with serine, asparagine, histidine, proline, lysine, glutamic acid, cysteine, glutamine, or methionine. Specifically, the polypeptide may be a polypeptide consisting of an amino acid sequence of any one of SEQ ID NO: 3 to SEQ ID NO: 20, or an amino acid sequence having a homology or identity thereto of 70% or more, specifically 80% or more, more specifically 85% or more, even more specifically 90% or more, even more specifically 95% or more, and even more specifically 99% or more, but is not limited thereto as long as it has an ability to export putrescine by substitution of alanine at position 152 with other amino acids. Additionally, it should be interpreted that, as an amino acid sequence having such a homology or identity, an amino acid sequence with deletion, modification, substitution, or addition of a part of the sequence also falls within the scope of the present disclosure as long as the amino acid sequence has a biological activity substantially identical or corresponding to the polypeptide consisting of the amino acid sequence of any one of SEQ ID NO: 3 to SEQ ID NO: 20.

As used herein, the term "ornithine-based product" refers to a material which can be biosynthesized from ornithine as a precursor. Specifically, examples of the materials that can be produced by the ornithine cycle include putrescine, citrulline, proline, and arginine, but the material is not limited thereto, as long as it can be biosynthesized from ornithine as a precursor. For example, the ornithine-based product may be putrescine and arginine. Additionally, any material which can be synthesized from ornithine as a precursor and exported by the novel polypeptide having an ability to export an ornithine-based product of the present disclosure, may be included without limitation.

Another aspect of the present disclosure provides a polynucleotide encoding the polypeptide having an ability to export an ornithine-based product.

The polynucleotide may include a polynucleotide encoding a polypeptide having an amino acid sequence of any one of SEQ ID NO: 3 to SEQ ID NO: 20, or a polypeptide having a homology or identity thereto of 70% or more, specifically 80% or more, more specifically 85% or more, even more specifically 90% or more, even more specifically 95% or more, and even more specifically 99% or more, but is not limited thereto, as long as it has an activity similar to the polypeptide having an ability to export an ornithine-based product. Additionally, it is apparent that due to codon degeneracy, polynucleotides which can be translated into the protein consisting of the amino acid sequence of SEQ ID NO: 1 or proteins having a homology or identity thereto can also be included. Alternatively, a probe which can be prepared from a known gene sequence, for example, any sequence which hybridizes with a sequence complementary to all or part of the nucleotide sequence under stringent conditions to encode a protein having the activity of the protein consisting of the amino acid sequence of SEQ ID NO: 1, may be included without limitation. The sequence having a homology or identity may exclude a sequence having a homology of 100% within the range above, or may be a sequence having a homology of less than 100%.

The "stringent conditions" refer to conditions under which specific hybridization between polynucleotides is allowed. Such conditions are specifically disclosed in the literature (e.g., J. Sambrook et al.). For example, the stringent conditions may include conditions under which genes having a high homology or identity, a homology or identity of 80% or more, specifically 85% or more, more specifically 90% or more, even more specifically 95% or more, even more specifically 97% or more, and even more specifically 99% or more, hybridize with each other, while genes having a homology or identity lower than the above homology or identity do not hybridize with each other; or may include ordinary washing conditions of Southern hybridization, i.e., washing once, specifically two or three times, at a salt concentration and a temperature corresponding to 60° C., 1∴SSC, and 0.1% SDS; specifically 60° C., 0.1×SSC, and 0.1% SDS; and more specifically 68° C., 0.1×SSC, and 0.1% SDS.

Hybridization requires that two nucleic acids have complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the present disclosure may also include an isolated nucleic acid fragment complementary to the entire sequence as well as a nucleic acid sequence substantially similar thereto.

Specifically, the polynucleotide having homology may be detected using hybridization conditions including a hybridization step at a $T_m$ value of 55° C. under the above-described conditions. Additionally, the $T_m$ value may be 60° C., 63° C., or 65° C., but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art (Sambrook et al., supra, 9.50-9.51, 11.7-11.8).

As used herein, the term "homology" refers to the degree of correspondence between two given amino acid sequences or nucleotide sequences, and may be expressed as a percentage. In the present disclosure, a homologous sequence having an activity which is identical or similar to that of the given amino acid sequence or nucleotide sequence may be indicated in terms of "% homology".

As used herein, the term "identity" refers to the degree of relevance between two given amino acid sequences or nucleotide sequences. In some cases, the identity is determined by the correspondence between strings of such sequences.

The terms "homology" and "identity" are often used interchangeably with each other.

The sequence homology or identity of conserved polynucleotides or polypeptides may be determined by standard alignment algorithms and can be used together with default gap penalty established by the program being used. Substantially, homologous or identical polynucleotides or polypeptides are generally expected to hybridize to all or at least about 50%, about 60%, about 70%, about 80%, about 85% or about 90% of the entire length of the target polynucleotides or polypeptides under moderate or high stringent conditions. Polynucleotides that contain degenerate codons instead of codons are also considered in the hybridizing polynucleotides.

Whether any two polynucleotide or polypeptide sequences have a homology or identity of at least 50%, 55%, 60%, 65% 70%, 75%, 80%, 85%, 90%, 95%, 96%, 97%, 98% or 99% with each other, it may be determined by a known computer algorithm such as the "FASTA" program (e.g., Pearson et al., (1988) *Proc. Natl. Acad. Sci. USA* 85: 2444) using default parameters. Alternatively, it may be determined by the Needleman-Wunsch algorithm (Needleman and Wunsch, 1970, *J. Mol. Biol.* 48: 443-453), which is performed using the Needleman program of the EMBOSS package (EMBOSS: The European Molecular Biology Open Software Suite, Rice et al., 2000, *Trends Genet.* 16: 276-277) (preferably, version 5.0.0 or versions thereafter) (GCG program package (Devereux, J., et al., *Nucleic Acids Research* 12: 387 (1984)), BLASTP, BLASTN, FASTA (Atschul, [S.] [F.,] [ET AL., *J. MOLEC BIOL* 215]: 403 (1990); Guide to Huge Computers, Martin J. Bishop, [ED.,] Academic Press, San Diego, 1994, and [CARILLO ETA/.] (1988) SIAM *J Applied Math* 48: 1073). For example, the homology or identity may be determined using BLAST or ClustalW of the National Center for Biotechnology Information (NCBI).

The homology or identity of polynucleotides or polypeptides may be determined by comparing sequence information using, for example, the GAP computer program, such as Needleman et al. (1970), *J Mol Biol.* 48: 443 as disclosed in Smith and Waterman, *Adv. Appl. Math* (1981) 2:482. In summary, the GAP program defines the homology or identity as the value obtained by dividing the number of similarly aligned symbols (i.e, nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to the comparison between polypeptides or polynucleotides.

Still another aspect of the present invention provides a vector comprising the polynucleotide.

As used herein, the term "vector" refers to a DNA construct containing the nucleotide sequence of a polynucleotide encoding the target polypeptide, which is operably linked to a suitable regulatory sequence such that the target polypeptide can be expressed in an appropriate host. The regulatory sequence may include a promoter capable of initiating transcription, any operator sequence for the control of the transcription, a sequence encoding an appropriate mRNA ribosome-binding domain, and a sequence regulating the termination of transcription and translation. After being transformed into a suitable host cell, the vector may be replicated or function irrespective of the host genome, and may be integrated into the host genome itself.

The vector used in the present disclosure is not particularly limited as long as it can be replicated in a host cell, and any vector known in the art may be used. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc. may be used. The vector that can be used in the present disclosure is not particularly limited, and a known expression vector may be used. Specifically, the vectors pDZ, pACYC177, pACYC184, pCL, pECCG117, pUC19, pBR322, pMW118, pCC1BAC, etc. may be used.

In an embodiment, a polynucleotide encoding a target polypeptide in the chromosome may be replaced with a modified polynucleotide through a vector for intracellular chromosome insertion. The insertion of the polynucleotide into the chromosome may be performed by any method known in the art, for example, homologous recombination, but is not limited thereto.

As used herein, the term "transformation" refers to a process of introducing a vector comprising a polynucleotide encoding a target polypeptide into a host cell, thereby enabling expression of the polypeptide encoded by the polynucleotide in the host cell. As long as the transformed polynucleotide can be expressed in the host cell, it does not matter whether it is inserted into the chromosome of a host cell and located therein or located outside the chromosome, and both cases may be included. For example, the transformation may be carried out via electroporation, calcium phosphate ($CaPO_4$) precipitation, calcium chloride ($CaCl_2$) precipitation, microinjection, a polyethylene glycol (PEG) technique, a DEAE-dextran technique, a cationic liposome technique, a lithium acetate-DMSO technique, etc., but the method is not limited thereto. Additionally, the polynucleotide includes DNA and RNA which encode a target polypeptide. The polynucleotide may be introduced in any form as long as it can be introduced into a host cell and expressed therein. For example, the polynucleotide may be introduced into a host cell in the form of an expression cassette, which is a gene construction including all elements necessary for self-expression. The expression cassette may conventionally include a promoter operably linked to the polynucleotide, a terminator, a ribosome-binding domain, and a stop codon. The expression cassette may be in the form of an expression vector capable of self-replication. Additionally, the polynucleotide may be introduced into a host cell as it is and operably linked to a sequence necessary for its expression in the host cell, but is not limited thereto.

Further, as used above, the term "operably linked" refers to a functional linkage between the above gene sequence and a promoter sequence which initiates and mediates the transcription of the polynucleotide encoding the target polypeptide of the present disclosure.

Still another aspect of the present disclosure provides a microorganism producing an ornithine-based product, comprising the polypeptide having an ability to export an ornithine-based product or having an enhanced activity thereof.

Specifically, the present disclosure provides a microorganism of the genus *Corynebacterium* producing putrescine or arginine, including the polypeptide having an ability to export an ornithine-based product or having an enhanced activity thereof.

As used herein, the term "microorganism" includes all of wild-type microorganisms, or naturally or artificially genetically modified microorganisms, and it may be a microorganism in which a particular mechanism is weakened or enhanced due to insertion of a foreign gene, or enhancement or inactivation of the activity of an endogenous gene.

As used herein, the term "microorganism of the genus *Corynebacterium*" may be specifically *Corynebacterium glutamicum, Corynebacterium ammoniagenes, Brevibacterium lactofermentum, Brevibacterium flavum, Corynebacterium thermoaminogenes, Corynebacterium efficiens*, etc., but is not limited thereto. More specifically, the microorganisms of the genus *Corynebacterium* in the present disclosure may be *Corynebacterium glutamicum*, the cell growth and survival of which are hardly affected even when exposed to a high concentration of putrescine or arginine.

As used herein, the term "microorganism of the genus *Corynebacterium* producing an ornithine-based product" refers to a microorganism of the genus *Corynebacterium* having an ability to produce an ornithine-based product naturally or via modification. The microorganism of the genus *Corynebacterium* producing an ornithine-based product may be, but is not particularly limited to, those modified such that the activity of at least one selected from the group consisting of, for example, acetylglutamate synthase, which converts glutamate to N-acetylglutamate, or ornithine acetyltransferase (argJ), which converts N-acetylornithine to ornithine, acetylglutamate kinase (ArgB), which converts N-acetylglutamate to N-acetylglutamyl phosphate, acetyl-gamma-glutamyl-phosphate reductase (ArgC), which converts N-acetylglutamyl phosphate to N-acetylglutamate semialdehyde, and acetylornithine aminotransferase (ArgD), which converts N-acetylglutamate semialdehyde to N-acetylornithine is increased compared to the endogenous activity thereof, in order to enhance the biosynthetic pathway from glutamate to ornithine, thereby improving ornithine productivity.

As used herein, the term "microorganism of the genus *Corynebacterium* producing putrescine or arginine" refers to a microorganism of the genus *Corynebacterium* having an ability to produce putrescine or arginine naturally or via modification. The microorganism of the genus *Corynebacterium* does not produce putrescine, can produce arginine, but the productivity of arginine is remarkably low. Therefore, as used herein, the microorganism of the genus *Corynebacterium* producing putrescine or arginine refers to a native strain itself or a microorganism of the genus *Corynebacterium* in which a foreign gene involved in the putrescine or arginine production mechanism is inserted, or the activity of an endogenous gene is enhanced or weakened, so as to have an improved productivity of putrescine or arginine.

Additionally, the microorganism producing putrescine may be those further modified such that the activity of at least one selected from the group consisting of ornithine carbamoyltransferase (ArgF), which is involved in the synthesis of arginine from ornithine, a protein involved in glutamate export, and acetyltransferase, which acetylates putrescine, is weakened compared to the endogenous activity thereof, and/or may be those modified such that an ornithine decarboxylase (ODC) activity is introduced.

Further, the microorganism producing arginine may be those further modified such that the activity of at least one selected from the group consisting of ornithine carbamoyltransfrase, (ArgF), which is involved in the synthesis of arginine from ornithine, argininosuccinate synthase (argG), argininosuccinate lyase (argH), aspartate ammonia lyase, and aspartate aminotransferase is enhanced, compared to the endogenous activity thereof.

As used herein, the term "enhancement" of activity of a protein means that the activity of a protein is introduced, or the activity is enhanced as compared with the endogenous activity thereof. The "introduction" of the activity means that the activity of a specific polypeptide that the microorganism did not originally have is naturally or artificially expressed.

As used herein, the term "increase" in the activity of a protein as compared with the endogenous activity thereof means that the activity of a protein is improved as compared with the endogenous activity of a protein possessed by a microorganism, or the activity of a non-modified protein before transformation. The "endogenous activity" refers to the activity of a specific protein originally possessed by the parental strain or a non-modified microorganism prior to transformation thereof, when the traits of the microorganism are altered through genetic modification due to natural or artificial factors, and it can be interchangeably used with the activity before transformation.

Specifically, the enhancement of activity in the present disclosure may be performed by the following methods:

1) a method for increasing the copy number of the polynucleotide encoding the protein;

2) a method for modifying an expression regulatory sequence such that the expression of the polynucleotide is increased;

3) a method for modifying the polynucleotide sequence on a chromosome such that the activity of the protein is enhanced;

4) a method for introducing a foreign polynucleotide exhibiting the activity of the protein or a modified polynucleotide in which the codons of the above polynucleotide have been optimized; and 5) a method for modification to enhance the activity by a combination of the above methods, but the method is not limited thereto.

The increasing of the copy number of the polynucleotide in method 1) above may be performed in the form in which the polynucleotide is operably linked to a vector, or by inserting into a chromosome of a host cell, but is not particularly limited thereto. Specifically, it may be performed by operably linking the polynucleotide encoding the protein of the present disclosure to a vector which can replicate and function regardless of the host cell, and introducing the same into the host cell. Alternatively, it may be performed by a method for increasing the copy number of the polynucleotide in the chromosome of the host cell by operably linking the polynucleotide to a vector which can insert the polynucleotide into the chromosome of the host cell, and introducing the same into the host cell.

Next, the modification of an expression regulatory sequence such that the expression of the polynucleotide is increased in method 2) may be performed by inducing a modification in the sequence through deletion, insertion, or non-conservative or conservative substitution of a nucleic acid sequence, or a combination thereof so as to further enhance the activity of the expression regulatory sequence, or by replacing with a nucleic acid sequence having a stronger activity, but is not particularly limited thereto. Additionally, the expression regulatory sequence may include a promoter, an operator sequence, a sequence encoding a ribosome-binding domain, a sequence regulating the termination of transcription and translation, etc., but is not particularly limited thereto.

A strong heterologous promoter may be linked to the upstream region of the expression unit of the polynucleotide instead of the original promoter. Examples of the strong promoter include CJ7 promoter (Korean Patent No. 0620092 and International Publication No. WO2006/065095), lysCP1 promoter (International Publication No. WO2009/096689), EF-Tu promoter, groEL promoter, aceA or aceB promoter, etc., but the strong promoter is not limited thereto. Further, the modification of the polynucleotide sequence on a chromosome in method 3) may be performed by inducing a modification in the expression regulatory sequence through deletion, insertion, or non-conservative or conservative substitution of a nucleic acid sequence, or a combination thereof so as to further enhance the activity of the polynucleotide sequence, or by replacing the polynucleotide sequence with a polynucleotide sequence modified to have a stronger activity, but is not particularly limited thereto.

Additionally, the introduction a foreign polynucleotide sequence in method 4) may be performed by introducing into a host cell a foreign polynucleotide encoding a protein that exhibits an activity identical or similar to that of the protein above, or a modified polynucleotide in which the codons of the foreign polynucleotide have been optimized. The foreign polynucleotide may be used without limitation by its origin or sequence as long as it exhibits an activity identical or similar to that of the protein. Further, the foreign polynucleotide may be introduced into a host cell after optimization of its codons so as to achieve the optimized transcription and translation in the host cell. The introduction may be performed by those skilled in the art by selecting a suitable transformation method known in the art, and a protein can be produced as the introduced polynucleotides are expressed in the host cell, thereby increasing its activity.

Finally, the method for modification to enhance the activity by a combination of methods 1) to 4) in method 5) may be performed by a combined application of at least one of the following methods: increasing the copy number of the polynucleotide encoding the protein, modifying an expression regulatory sequence such that the expression of the polynucleotide is increased, modifying the polynucleotide sequence on a chromosome, and modifying a foreign polynucleotide exhibiting the activity of the protein or a codon-optimized modified polynucleotide thereof.

As used herein, the term "inactivation" of the activity of a protein includes both reduction in activity due to weakening or having no activity at all, as compared to the endogenous activity thereof.

The inactivation of the activity of a protein may be achieved by various methods well known in the art. Examples of the methods include a method of deleting a part or the entirety of a gene encoding the protein on a chromosome, including the case where the activity of the protein is eliminated; a method of replacing the gene encoding the protein on the chromosome with a gene mutated so as to reduce the enzyme activity; a method of introducing a modification into an expression regulatory sequence of the gene encoding the protein on the chromosome; a method of replacing an expression regulatory sequence of the gene encoding the protein with a sequence having a weak activity or no activity (e.g., a method of replacing the gene promoter with a promoter weaker than the endogenous promoter); a method of deleting a part or the entirety of a gene encoding the protein on a chromosome; a method of introducing an antisense oligonucleotide that binds complementarily to the transcript of the gene on the chromosome to inhibit the translation of the mRNA into the protein (e.g., antisense RNA); a method of artificially adding a sequence complementary to the upstream of the SD sequence of the gene encoding the enzyme to form a secondary structure, thereby making the adhesion of ribosome impossible; and a method of reverse transcription engineering (RTE), which adds a promoter to the 3' end of the open reading frame (ORF) of the corresponding sequence so as to be reverse-transcribed, or a combination thereof, but are not particularly limited thereto.

Specifically, the method of deleting a part or the entirety of a gene encoding the protein may be performed by replacing the polynucleotide encoding the endogenous target protein within the chromosome with a polynucleotide having a partially deleted nucleic acid sequence or a marker gene through a vector for chromosomal insertion into microorganisms. In an embodiment, a method for deleting a gene by homologous recombination may be used, but is not limited thereto. Additionally, as used herein, the term "part", although it may vary depending on the kinds of polynucleotide and may be appropriately selected by those skilled in the art, may specifically refer to 1 to 300 nucleotides, more specifically 1 to 100 nucleotides, and even more specifically 1 to 50 nucleotides, but is not particularly limited thereto.

Additionally, the method of modifying an expression regulatory sequence may be performed by inducing a modification in the expression regulatory sequence through deletion, insertion, conservative or non-conservative substitution, or a combination thereof so as to further weaken the activity of the expression regulatory sequence; or by replacing the sequence with a nucleic acid sequence having a weaker activity. The expression regulatory sequence may include a promoter, an operator sequence, a sequence encoding a ribosome-binding domain, and a sequence regulating the termination of transcription and translation, but is not limited thereto.

Further, the method of modifying the gene sequence on the chromosome may be performed by inducing a modification in the gene sequence through deletion, insertion, conservative or non-conservative substitution, or a combination thereof so as to further inactivate the activity of the protein; or by replacing the sequence with a gene sequence modified to further inactivate the activity, or a gene sequence modified to have no activity at all, but is not limited thereto.

Still another aspect of the present disclosure provides a method for producing an ornithine-based product, comprising:

(i) culturing a microorganism producing an ornithine-based product comprising the polypeptide having an ability to export an ornithine-based product or having an enhanced activity thereof in a medium; and (ii) recovering the ornithine-based product from the microorganism or the medium obtained above.

In a specific embodiment, the present disclosure provides a method for producing putrescine, comprising:

(i) culturing a microorganism producing putrescine comprising the polypeptide having an ability to export an ornithine-based product or having an enhanced activity thereof in a medium; and (ii) recovering putrescine from the microorganism or the medium obtained above.

In another specific embodiment, the present disclosure provides a method for producing L-arginine, comprising:

(i) culturing a microorganism producing L-arginine comprising the polypeptide having an ability to export an ornithine-based product or having an enhanced activity thereof in a medium; and (ii) recovering L-arginine from the microorganism or the medium obtained above.

The polypeptide having an ability to export an ornithine-base product and/or the microorganism producing an ornithine-based product are as described above.

In the method above, the culturing of the microorganism may be performed by a known batch culture method, continuous culture method, fed-batch culture method, etc., but is not particularly limited thereto. In particular, with respect to the culture conditions, the pH of the culture may be adjusted to a suitable pH (e.g., pH 5 to 9, specifically pH 6 to 8, and most specifically pH 6.8) using a basic compound (e.g., sodium hydroxide, potassium hydroxide, or ammonia) or an acidic compound (e.g., phosphoric acid or sulfuric acid). Additionally, oxygen or oxygen-containing gas mixture may be injected into the culture in order to maintain an aerobic state. The culture temperature may be maintained at 20° C. to 45° C., specifically at 25° C. to 40° C., and the culturing may be performed for about 10 hours to 160 hours, but the culture is not limited to the above. The putrescine produced by the culture may be secreted in the medium or may remain in the cells.

Additionally, as a carbon source for the culture medium to be used, sugars and carbohydrates (e. g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but is not limited thereto. As a nitrogen source, nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but is not limited thereto. As a phosphorus source, potassium dihydrogen phosphate, dipotassium hydrogen phosphate, corresponding sodium-containing salts thereof, etc. may be used alone or in combination, but is not limited thereto. In addition, essential growth-promoting materials such as other metal salts (e.g., magnesium sulfate or iron sulfate), amino acids, vitamins, etc. may be contained in the medium.

In the method for recovering the ornithine-based product produced in the culturing step of the present disclosure, the desired products may be collected from the cultured microorganism or medium using an appropriate method known in the art. For example, centrifugation, filtration, anion-exchange chromatography, crystallization, HPLC, etc. may be used, but is not limited thereto. Additionally, the method for recovering the ornithine-based product may further include a purification process using an appropriate method known in the art.

DETAILED DESCRIPTION OF PREFERRED EMBODIMENTS

The present disclosure will be described in more detail through exemplary embodiments. However, these exemplary embodiments are given for illustrative purposes only, and are not intended to limit the scope of the present disclosure.

EXAMPLE 1

Confirmation of Ability to Export Arginine of Putrescine-Exporting Protein

It has been found that NCgl2522, a gene of *Corynebacterium glutamicum*, has an ability to export putrescine (Korean Patent Application Publication No. 2014-0115244). To this end, the following experiment was conducted to confirm whether NCgl2522 can also export citrulline, proline, and arginine, which can be biosynthesized from ornithine as a starting material, in addition to putrescine.

Specifically, it was confirmed whether NCgl2522 has an ability to export arginine as a representative example, among the products that can be biosynthesized from ornithine as a starting material.

<1-1> Construction of Arginine-Producing Strain-Based Vectors and Strains Having Enhanced NCgl2522 Activity In order to enhance the NCgl2522 activity in the wild-type ATCC21831 strain and KCCM10741P (Korean Patent No. 10-0791659) having an arginine-producing ability, the CJ7 promoter (WO 2006/065095A) was introduced to the upstream of the initiation codon of NCgl2522 within the chromosome.

A homologous recombinant fragment, which includes the CJ7 promoter disclosed in WO 2006/065095A and in which both ends of the promoter have the original NCgl2522 sequence on the chromosome, was obtained. Specifically, the 5'-end region of the CJ7 promoter was obtained by performing PCR using a primer pair of SEQ ID NOS: 63 and 64 shown in Table 1, based on the genomic DNA of the *Corynebacterium glutamicum* ATCC21831 or KCCM10741P as a template. In particular, the PCR reaction was performed by repeating 30 cycles of denaturation at 94° C. for 30 seconds, annealing at 55° C. for 30 seconds, and extension at 72° C. for 30 seconds. Additionally, the CJ7 promoter region was obtained by performing PCR under the same conditions using a primer pair of SEQ ID NOS: 65 and 66 shown in Table 1, and the 3'-end region of the CJ7 promoter was obtained by performing PCR using a primer pair of SEQ ID NOS: 67 and 68 under the same conditions, based on the genomic DNA of the *Corynebacterium glutamicum* ATCC21831 or KCCM10741P as a template. The primers used in the substitution of promoters are shown in Table 1 below.

TABLE 1

| Primers | Sequence (5'→3') |
|---|---|
| NCgl2522-L5 (SEQ ID NO: 63) | TGCAGGTCGACTCTAGA GTTCTGCGTAGCTGTGTGCC |
| NCgl2522-L3 (SEQ ID NO: 64) | GATGTTTCT GGATCGTAACTGTAACGAATGG |
| CJ7-F (SEQ ID NO: 65) | AGAAACATCCCAGCGCTACTAATA |
| CJ7-R (SEQ ID NO: 66) | AGTGTTTCCTTTCGTTGGGTACG |
| NCgl2522-R5 (SEQ ID NO: 67) | CAACGAAAGGAAACACT ATGATTTCAGAAACTTTGCAGGCG |
| NCgl2522-R3 (SEQ ID NO: 68) | TCGGTACCCGGGGATCC CACAAAAAGCGTAGCGATCAACG |

Each of the PCR products obtained above was subjected to fusion cloning into the pDZ vector treated with BamHI and XbaI. The fusion cloning was performed at 50° C. for 10 minutes using the In-Fusion® HD Cloning Kit (Clontech Laboratories, Inc.), and the thus-obtained plasmids were named pDZ-P(CJ7)-NCgl2522-21831 and pDZ-P(CJ7)-NCgl2522-10741P, respectively.

The plasmids pDZ-P(CJ7)-NCgl2522-21831 and pDZ-P(CJ7)-NCgl2522-10741P prepared above were respectively introduced into ATCC21831 and KCCM10741P, which are arginine-producing strains, via electroporation to obtain transformants, and the thus-obtained transformants were plated on BHIS plate media (37 g/L of Braine heart infusion, 91 g/L of sorbitol, and 2% agar) containing kanamycin (25 µg/mL) and X-gal (5-bromo-4-chloro-3-indolin-D-galactoside) and cultured to form colonies. Among the thus-formed colonies, the strains introduced with the plasmid pDZ-P(CJ7)-NCgl2522-21831 or pDZ-P(CJ7)-NCgl2522-10741P were selected.

The selected strains were cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from 10' to 10', plated on solid media containing X-gal, and cultured to form colonies. Among the thus-formed colonies, white colonies which appeared at a relatively low rate were selected, thereby finally selecting the strains, in which the promoter of the NCgl2522 gene was substituted with the CJ7 promoter by a secondary crossover. The finally selected strains were subjected to PCR using a primer pair of SEQ ID NOS: 65 and 68 shown in Table 1, and the thus-obtained products were applied to sequencing. As a result, it was confirmed that the CJ7 promoter was introduced into the upstream of the initiation codon of NCgl2522 within the chromosome. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named ATCC21831_Pcj 7 Ncgl2522 and KCCM10741P_Pcj 7 NCgl2522, respectively.

<1-2> Confirmation of Arginine-Producing Ability of Arginine-Producing Strain-Based Strains Having Enhanced NCgl2522 Activity In order to confirm the effect of the NCgl2522 gene on the ability to export arginine, one of the ornithine-based products, the arginine-producing ability was compared among the modified strains of *Corynebacterium glutamicum* ATCC21831_Pcj7 Ncgl2522 and KCCM10741P_Pcj7 NCgl2522 prepared in Example 1 above.

As the control groups, *Corynebacterium glutamicum* ATCC21831 and KCCM10741P, which are the parent strains, were used, and one platinum loop of each strain was inoculated into a 250-mL corner-baffled flask containing 25 mL of production media [6% glucose, 3% ammonium sulfate, 0.1% monopotassium phosphate, 0.2% magnesium sulfate heptahydrate, 1.5% corn steep liquor (CSL), 1% NaCl, 0.5% yeast extract, and 100 µg/L of biotin at pH7.2] and cultured at 30° C. at a rate of 200 rpm for 48 hours to produce arginine. After completion of the culture, the arginine production was measured by HPLC. The results are shown in Table 2 below.

TABLE 2

| Strains | OD | Arginine Concentration (g/L) | Ornithine Concentration (g/L) | Arginine Fold (%) |
|---|---|---|---|---|
| KCCM10741P | 91 | 3.0 | 0.3 | 100 |
| KCCM10741P_Pcj7 Ncgl2522 | 72 | 3.6 | 0.4 | 120 |
| ATCC21831 | 102 | 4.2 | 0.3 | 100 |
| ATCC21831_Pcj7 Ncgl2522 | 86 | 4.8 | 0.4 | 114 |

As shown in Table 2, when the promoter of the NCgl2522 gene in KCCM10741P and ATCC21831 was enhanced by substitution with the CJ7 promoter, the modified strains of *Corynebacterium glutamicum* showed an increase in the arginine production by 20% and 14% as compared to the parent strains, respectively. Additionally, it was confirmed that the concentration of ornithine, a reactant before conversion to arginine, was also increased in the modified strains as compared to the parent strains.

Based on these findings, it was confirmed that the NCgl2522 gene is not only a gene for exporting putrescine, but also has an ability to export products including ornithine which are biosynthesized from ornithine as a starting material. Additionally, it can be interpreted from the above results that the NCgl2522 gene and the variants of the present disclosure can be very useful in the production of ornithine-based products using biomass.

EXAMPLE 2

Construction of Library of Gene Variants Encoding Putrescine-Exporting Protein and Establishment of Effective Modification In order to increase the activity of the ornithine-based product-exporting protein, the present inventors constructed variants for NCgl2522 (Korea Patent No. 10-1607741), a gene encoding the putrescine-exporting protein.

Specifically, in order to construct a library of the NCgl2522 gene variants, a random mutagenesis PCR (JENA error-prone PCR) was performed using a specific primer pair of SEQ ID NOS: 21 and 22 excluding the initiation codon of ORF of the NCgl2522 gene shown in Table 2, based on the genomic DNA of *Corynebacterium glutamicum* ATCC13032 as a template.

TABLE 3

| Primer | Sequence (5'→3') |
|---|---|
| 13032-putE-EF-FX (SEQ ID NO: 21) | CCGGGGATCCTCTAGA ACTTCAGAAACCTTACAGGC |
| 13032-putE-EF-RX (SEQ ID NO: 22) | GCAGGTCGACTCTAGA CTAGTGCGCATTATTGGCTC |

The thus-prepared mutant gene fragments were subjected to fusion cloning into the pDZ vector cleaved with XbaI. The fusion cloning was performed at 50° C. for 10 minutes using the In-Fusion® HD Cloning Kit (Clontech Laboratories, Inc.), thereby completing the construction of plasmid libraries of pDZ-N2522 variants.

The thus-constructed recombinant plasmid libraries were screened via high throughput screening (HTS). In particular, the platform strain used for screening was KCCM11240P, which is a *Corynebacterium glutamicum*-derived recombinant microorganism capable of producing putrescine (Korean Patent No. 10-1493585).

Specifically, in order to obtain variants with an improved activity for exporting putrescine, the thus-constructed plasmid libraries were introduced into KCCM11240P via electroporation to obtain transformants, and the thus-obtained transformants were plated on BHIS plate media (37 g/L of Braine heart infusion, 91 g/L of sorbitol, and 2% agar) containing kanamycin (25 μg/mL) and X-gal (5-bromo-4-chloro-3-indolin-D-galactoside) and cultured to form colonies. Among the thus-formed colonies, the strains introduced with the plasmid pDZ-N2522 variant libraries were selected.

The selected strains were cultured by shaking in a 96 deep well plate along with titer media (2 g/L of glucose, 0.4 g/L of MgSO$_4$.7H$_2$O, 0.8 g/L of MgCl$_2$, 1 g/L of KH$_2$PO$_4$, 4 g/L of (NH$_4$)$_2$SO$_4$, 0.48 g/L of soybean protein hydrolysate, 0.01 g/L of MnSO$_4$.7H$_2$O, 200 μg/L of thiamine HCl, 200 μg/L of biotin, 0.01 g/L of FeSO$_4$.7H$_2$O, 1 mM arginine, and 25 μg/mL of kanamycin at pH 7.2), and the concentration of putrescine produced in each culture was measured, and then one transformant with the greatest increase in putrescine productivity compared to the control was selected. Subsequently, it was confirmed as to which modification was induced in the amino acid sequence of the NCgl2522 protein for the selected transformant. The sequence of the Ncgl2522 variant was confirmed as follows: a homologous recombinant fragment was obtained by performing colony PCR using a primer pair of SEQ ID NOS: 21 and 22, based on the transformant including the corresponding variants, followed by applying the product to genome sequencing using a primer of SEQ ID NO: 7. In particular, the PCR reaction was performed by repeating 30 cycles of denaturation at 95° C. for 30 seconds, annealing at 55° C. for 30 seconds, and extension at 72° C. for 1 minute.

As a result, it was confirmed that the selected NCgl2522 variant was modified such that the alanine (Ala), which is the amino acid residue at position 152 from the N-terminus of the NCgl2522 amino acid sequence (SEQ ID NO: 1) of *Corynebacterium glutamicum* ATCC13032 was substituted with serine (Ser), and was named NCgl2522_M1 (SEQ ID NO: 3).

EXAMPLE 3

Establishment of Various Variants in Which Amino Acid Residue at Position 152 of Gene Encoding Putrescine-Exporting Protein is Substituted Based on the NCgl2522_M1 variant prepared in Example 2, the present inventors realized that the amino acid residue at position 152 from the N-terminus is important for the activity of the NCgl2522 protein. Accordingly, various variants, in which the amino acid residue at position 152 of the NCgl2522 protein was substituted with other amino acid residues, were prepared.

Specifically, a homologous recombinant fragment was obtained using a specific primer pair of SEQ ID NOS: 21 and 22 excluding the initiation codon of ORF of NCgl2522 gene, based on the genomic DNA of *Corynebacterium glutamicum* ATCC13032 as a template. In particular, the PCR reaction was performed by repeating 30 cycles of denaturation at 95° C. for 30 seconds, annealing at 55° C. for 30 seconds, and extension at 72° C. for 30 seconds.

Subsequently, the PCR product obtained above was subjected to fusion cloning into the pDZ vector treated with XbaI. The fusion cloning was performed using the In-Fusion® HD Cloning Kit (Clontech Laboratories, Inc.), and the thus-obtained plasmid was named pDZ-NCgl2522_A152.

Then, in order to induce a random mutagenesis on the amino acid residue at position 152 of NCgl2522, a plasmid library for the pDZ-NCgl2522 A152 variant was completed by performing PCR using a primer pair of SEQ ID NOS: 23 and 24 shown in Table 4, based on the plasmid pDZ-NCgl2522_A152 constructed above as a template. In particular, the PCR reaction was performed by repeating 25 cycles of denaturation at 95° C. for 30 seconds, annealing at 55° C. for 30 seconds, and extension at 72° C. for 5 minutes.

TABLE 4

| Primer | Sequence (5'→3') |
|---|---|
| SM_putE_A152-F (SEQ ID NO: 23) | TGGGGTTCCGTGNNKATTCTTGGCGCT |
| SM_putE_A152-R (SEQ ID NO: 24) | AGCGCCAAGAATMNNCACGGAACCCCA |

The thus-constructed recombinant plasmid libraries were screened via high throughput screening (HTS). In particular, the platform strain used for screening was KCCM11240P, which is a *Corynebacterium glutamicum*-derived recombinant microorganism capable of producing putrescine.

The constructed plasmid libraries were introduced into KCCM11240P via electroporation to obtain transformants, and the strains introduced with the plasmid pDZ-NCgl2522_A152 variant were selected in the same manner as in Example 2. Eight transformants with the greatest increase in putrescine productivity compared to the control group were selected, and it was confirmed as to which modifications were induced in the amino acid sequence of the NCgl2522 protein for each transformant, in the same manner as in Example 2.

As a result, variants in which alanine, the amino acid residue at position 152 from the N-terminus of the NCgl2522 amino acid sequence (SEQ ID NO: 1) of *Corynebacterium glutamicum* ATCC13032, was substituted with other amino acids, were confirmed. Among them, the variant, in which the amino acid residue at position 152 was substituted with asparagine, was named NCgl2522_M4 (SEQ ID NO: 6), the variant, in which the amino acid residue at position 152 was substituted with proline, was named NCgl2522_M5 (SEQ ID NO: 7), the variant, in which the amino acid residue at position 152 was substituted with lysine, was named NCgl2522_M6 (SEQ ID NO: 8), the variant, in which the amino acid residue at position 152 was substituted with glutamic acid, was named NCgl2522_M7 (SEQ ID NO: 9), the variant, in which the amino acid residue at position 152 was substituted with cysteine, was named NCgl2522_M8 (SEQ ID NO: 10), the variant, in which the amino acid residue at position 152 was substituted with glutamine, was named NCgl2522_M9 (SEQ ID NO: 11), and the variant, in which the amino acid residue at position 152 was substituted with methionine, was named NCgl2522_M10 (SEQ ID NO: 12).

Additionally, in order to confirm whether the effect of increasing putrescine productivity due to the modification can be applied to NCgl2522 proteins derived from different strains, various variants, in which the amino acid residue at position 152 of the NCgl2522 protein derived from *Corynebacterium glutamicum* ATCC13869 was substituted with other amino acid residues, were constructed.

Specifically, a homologous recombinant fragment was obtained using a specific primer pair of SEQ ID NOS: 21 and 22 excluding the initiation codon of ORF of NCgl2522 gene, based on the genomic DNA of *Corynebacterium glutamicum* ATCC13869 as a template. In particular, the PCR reaction was performed by repeating 30 cycles of denaturation at 95° C. for 30 seconds, annealing at 55° C. for 30 seconds, and extension at 72° C. for 30 seconds.

The PCR product obtained above was subjected to fusion cloning into the pDZ vector treated with XbaI. The fusion cloning was performed using the In-Fusion® HD Cloning Kit (Clontech Laboratories, Inc.), and the thus-obtained plasmid was named pDZ-13869-NCgl2522 A152.

Then, in order to induce a random mutagenesis on the amino acid residue at position 152 of NCgl2522, a plasmid library for the pDZ-13869-NCgl2522 A152 variant was completed by performing PCR using a primer pair of SEQ ID NOS: 23 and 24, based on the plasmid pDZ-13869-NCgl2522_A152 constructed above as a template. In particular, the PCR reaction was performed by repeating 25 cycles of denaturation at 95° C. for 30 seconds, annealing at 55° C. for 30 seconds, and extension at 72° C. for 5 minutes.

Subsequently, the thus-constructed recombinant plasmid libraries were screened via high throughput screening (HTS). In particular, the platform strain used for screening was DAB12-b, which is a *Corynebacterium glutamicum*-derived recombinant microorganism capable of producing putrescine. Then, the constructed plasmid libraries were introduced into DAB12-b via electroporation to obtain transformants, and the strains introduced with the plasmid pDZ-13869-NCgl2522_A152 variant were selected in the same manner as in Example 2.

As a result, nine variants, in which the amino acid residue at position 152 from the N-terminus of the NCgl2522 amino acid sequence (SEQ ID NO: 2) of *Corynebacterium glutamicum* ATCC13869 was substituted, were selected, as the NCgl2522 variants of *Corynebacterium glutamicum* ATCC13032. Among them, the variant in which alanine, the amino acid residue at position 152, was substituted with serine was named NCgl2522_M2 (SEQ ID NO: 4), the variant, in which the amino acid residue at position 152 was substituted with asparagine, was named NCgl2522_M11 (SEQ ID NO: 13), the variant, in which the amino acid residue at position 152 was substituted with histidine, was named NCgl2522_M12 (SEQ ID NO: 14), the variant, in which the amino acid residue at position 152 was substituted with proline, was named NCgl2522_M13 (SEQ ID NO: 15), the variant, in which the amino acid residue at position 152 was substituted with lysine, was named NCgl2522_M14 (SEQ ID NO: 16), the variant, in which the amino acid residue at position 152 was substituted with glutamic acid, was named NCgl2522_M15 (SEQ ID NO: 17), the variant, in which the amino acid residue at position 152 was substituted with cysteine, was named NCgl2522_M16 (SEQ ID NO: 18), the variant, in which the amino acid residue at position 152 was substituted with glutamine, was named NCgl2522_M17 (SEQ ID NO: 19), and the variant, in which the amino acid residue at position 152 was substituted with methionine, was named NCgl2522_M18 (SEQ ID NO: 20).

EXAMPLE 4

Construction of NCgl2522 Variant Strains and Confirmation of Putrescine-Producing Ability Thereof <4-1> Construction of NCgl2522 Variant Strains from ATCC13032-Based Putrescine-Producing Strain In order to increase the ability to export putrescine of the putrescine-producing strain, NCgl2522_M1, NCgl2522_M3, NCgl2522_M4, NCgl2522_M5, NCgl2522_M6, NCgl2522_M7, NCgl2522_M8, NCgl2522_M9 and NCgl2522_M10, which are variant of the NCgl2522 gene, were respectively introduced into the chromosome of the *Corynebacterium glutamicum* ATCC13032-based putrescine-producing strain.

Specifically, homologous recombinant fragments having a modified sequence of NCgl2522_M1, NCgl2522_M3, NCgl2522_M4, NCgl2522_M5, NCgl2522_M6, NCgl2522_M7, NCgl2522_M8, NCgl2522_M9, and NCgl2522_M10 were respectively obtained by performing PCR using primer pairs of SEQ ID NOS: 25 and 28, SEQ ID NOS: 26 and 27, SEQ ID NOS: 25 and 30, SEQ ID NOS: 26 and 29, SEQ ID NOS: 25 and 32, SEQ ID NOS: 26 and 31, SEQ ID NOS: 25 and 34, SEQ ID NOS: 26 and 33, SEQ ID NOS: 25 and 36, SEQ ID NOS: 26 and 35, SEQ ID NOS: 25 and 38, SEQ ID NOS: 26 and 37, SEQ ID NOS: 25 and 40, SEQ ID NOS: 26 and 39, SEQ ID NOS: 25 and 42, SEQ ID NOS: 26 and 41, SEQ ID NOS: 25 and 44, and SEQ ID NOS: 26 and 43 shown in Table 5, based on the genomic DNA of *Corynebacterium glutamicum* ATCC13032 as a template. In particular, the PCR reaction was performed by repeating 30 cycles of denaturation at 95° C. for 30 seconds, annealing at 55° C. for 30 seconds, and extension at 72° C. for 30 seconds.

TABLE 5

| Primer | Sequence (5'→3') |
|---|---|
| pDC-putE-up-FX (SEQ ID NO: 25) | CCGGGGATCCTCTAGAGTGGTCTCTTTC TGATCG |
| pDC-putE-down-RX (SEQ ID NO: 26) | GCAGGTCGACTCTAGAGCAATTCCTTG TCCCAGT |
| 13032_putE_A152S-F (SEQ ID NO: 27) | GGGTTCCGTG TCC ATTCTTGGCG |
| 13032_putE_A152S-R (SEQ ID NO: 28) | CGCCAAGAAT GGA CACGGAACCC |

TABLE 5-continued

| Primer | Sequence (5'→3') |
|---|---|
| 13032_putE_A152N-F (SEQ ID NO: 29) | GGGTTCCGTG AAT ATTCTTGGCG |
| 13032_putE_A152N-R (SEQ ID NO: 30) | CGCCAAGAAT ATT CACGGAACCC |
| 13032_putE_A152H-F (SEQ ID NO: 31) | GGGTTCCGTG CAT ATTCTTGGCG |
| 13032_putE_A152H-R (SEQ ID NO: 32) | CGCCAAGAAT ATG CACGGAACCC |
| 13032_putE_A152P-F (SEQ ID NO: 33) | GGGTTCCGTG CCT ATTCTTGGCG |
| 13032_putE_A152P-R (SEQ ID NO: 34) | CGCCAAGAAT AGG CACGGAACCC |
| 13032_putE_A152K-F (SEQ ID NO: 35) | GGGTTCCGTG AAG ATTCTTGGCG |
| 13032_putE_A152K-R (SEQ ID NO: 36) | CGCCAAGAAT CTT CACGGAACCC |
| 13032_putE_A152E-F (SEQ ID NO: 37) | GGGTTCCGTG GAG ATTCTTGGCG |
| 13032_putE_A152E-R (SEQ ID NO: 38) | CGCCAAGAAT CTC CACGGAACCC |
| 13032_putE_A152C-F (SEQ ID NO: 39) | GGGTTCCGTG TGT ATTCTTGGCG |
| 13032_putE_A152C-R (SEQ ID NO: 40) | CGCCAAGAAT ACA CACGGAACCC |
| 13032_putE_A152Q-F (SEQ ID NO: 41) | GGGTTCCGTG CAG ATTCTTGGCG |
| 13032_putE_A152Q-R (SEQ ID NO: 42) | CGCCAAGAAT CTG CACGGAACCC |
| 13032_putE_A152M-F (SEQ ID NO: 43) | GGGTTCCGTG ATG ATTCTTGGCG |
| 13032_putE_A152M-R (SEQ ID NO: 44) | CGCCAAGAAT CATC ACGGAACCC |

Each of the PCR products obtained above was subjected to fusion cloning into the pDZ vector treated with XbaI. The fusion cloning was performed using the In-Fusion® HD Cloning Kit (Clontech Laboratories, Inc.), and the thus-obtained plasmids were named pDZ-NCgl2522_M1, pDZ-NCgl2522_M3, pDZ-NCgl2522_M4, pDZ-NCgl2522_M5, pDZ-NCgl2522_M6, pDZ-NCgl2522_M7, pDZ-NCgl2522_M8, pDZ-NCgl2522_M9 and pDZ-NCgl2522_M10, respectively.

The plasmids pDZ-NCgl2522_M1, pDZ-NCgl2522_M3, pDZ-NCgl2522_M4, pDZ-NCgl2522_M5, pDZ-NCgl2522_M6, pDZ-NCgl2522_M7, pDZ-NCgl2522_M8, pDZ-NCgl2522_M9 and pDZ-NCgl2522_M10 prepared above were respectively introduced into KCCM11240P (Korean Patent Application Publication No. 2013-0082478), which is a *Corynebacterium glutamicum* ATCC13032-based putrescine-producing strain, via electroporation to obtain transformants, and the thus-obtained transformants were plated on BHIS plate media (37 g/L of Braine heart infusion, 91 g/L of sorbitol, and 2% agar) containing kanamycin (25 µg/mL) and X-gal (5-bromo-4-chloro-3-indolin-D-galactoside) and cultured to form colonies. Among the thus-formed colonies, the strains introduced with each plasmid were selected.

Each of the strains selected above was cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from $10^{-4}$ to $10^{-10}$, plated on solid media containing X-gal, and cultured to form colonies. Among the thus-formed colonies, white colonies which appeared at a relatively low rate were selected, thereby finally selecting the strains, in which the NCgl2522 gene was substituted with each of the variants by a secondary crossover. The finally selected strains were subjected to PCR using a primer pair of SEQ ID NOS: 25 and 26, and the thus-obtained products were applied to sequencing to confirm the substitution with each of the variants. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named KCCM11240P NCgl2522_M1, KCCM11240P NCgl2522_M3, KCCM11240P NCgl2522_M4, KCCM11240P NCgl2522_M5, KCCM11240P NCgl2522_M6, KCCM11240P NCgl2522_M7, KCCM11240P NCgl2522_M8, KCCM11240P NCgl2522_M9 and KCCM11240P NCgl2522_M10, respectively.

<4-2> Construction of NCgl2522 Variant Strains from ATCC13869-Based Putrescine-Producing Strain DAB12-a ΔNCgl1469 (Korean Patent Application Publication No. 2013-0082478), which is a *Corynebacterium glutamicum* ATCC13869-based putrescine-producing strain, was named DAB12-b. To this end, in order to increase the ability to export putrescine of the putrescine-producing strain, NCgl2522_M2, NCgl2522_M11, NCgl2522_M12, NCgl2522_M13, NCgl2522_M14, NCgl2522_M15, NCgl2522_M16, NCgl2522_M17 and NCgl2522_M18, which are variants of the NCgl2522 gene, were respectively introduced into the chromosome of the DAB12-b strain.

Specifically, homologous recombinant fragments having a modified sequence of NCgl2522_M2, NCgl2522_M11, NCgl2522_M12, NCgl2522_M13, NCgl2522_M14, NCgl2522_M15, NCgl2522_M16, NCgl2522_M17 and NCgl2522_M18 were respectively obtained by performing PCR using primer pairs of SEQ ID NOS: 25 and 46, SEQ ID NOS: 26 and 45, SEQ ID NOS: 25 and 48, SEQ ID NOS: 26 and 47, SEQ ID NOS: 25 and 50, SEQ ID NOS: 26 and 49, SEQ ID NOS: 25 and 52, SEQ ID NOS: 26 and 51, SEQ ID NOS: 25 and 54, SEQ ID NOS: 26 and 53, SEQ ID NOS: 25 and 56, SEQ ID NOS: 26 and 55, SEQ ID NOS: 25 and 58, SEQ ID NOS: 26 and 57, SEQ ID NOS: 25 and 50, SEQ ID NOS: 26 and 59, SEQ ID NOS: 25 and 62, and SEQ ID NOS: 26 and 61 shown in Tables 5 and 6, based on the genomic DNA of *Corynebacterium glutamicum* ATCC13869 as a template. In particular, the PCR reaction was performed by repeating 30 cycles of denaturation at 95° C. for 30 seconds, annealing at 55° C. for 30 seconds, and extension at 72° C. for 30 seconds.

TABLE 6

| Primer | Sequence (5'→3') |
|---|---|
| 13869_putE_A152S-F (SEQ ID NO: 45) | GGGTTCTGTG TCC ATTCTTGGCG |
| 13869_putE_A152S-R (SEQ ID NO: 46) | CGCCAAGAAT GGA CACAGAACCC |

TABLE 6-continued

| Primer | Sequence (5'→3') |
|---|---|
| 13869_putE_A152N-F (SEQ ID NO: 47) | GGGTTCTGTG AAT ATTCTTGGCG |
| 13869_putE_A152N-R (SEQ ID NO: 48) | CGCCAAGAAT ATT CACAGAACCC |
| 13869_putE_A152H-F (SEQ ID NO: 49) | GGGTTCTGTG CAT ATTCTTGGCG |
| 13869_putE_A152H-R (SEQ ID NO: 50) | CGCCAAGAAT ATG CACAGAACCC |
| 13869_putE_A152P-F (SEQ ID NO: 51) | GGGTTCTGTG CCT ATTCTTGGCG |
| 13869_putE_A152P-R (SEQ ID NO: 52) | CGCCAAGAAT AGG CACAGAACCC |
| 13869_putE_A152K-F (SEQ ID NO: 53) | GGGTTCTGTG AAG ATTCTTGGCG |
| 13869_putE_A152K-R (SEQ ID NO: 54) | CGCCAAGAAT CTT CACAGAACCC |
| 13869_putE_A152E-F (SEQ ID NO: 55) | GGGTTCTGTG GAG ATTCTTGGCG |
| 13869_putE_A152E-R (SEQ ID NO: 56) | CGCCAAGAAT CTC CACAGAACCC |
| 13869_putE_A152C-F (SEQ ID NO: 57) | GGGTTCTGTG TGT ATTCTTGGCG |
| 13869_putE_A152C-R (SEQ ID NO: 58) | CGCCAAGAAT ACA CACAGAACCC |
| 13869_putE_A152Q-F (SEQ ID NO: 59) | GGGTTCTGTG CAG ATTCTTGGCG |
| 13869_putE_A152Q-R (SEQ ID NO: 60) | CGCCAAGAAT CTG CACAGAACCC |
| 13869_putE_A152M-F (SEQ ID NO: 61) | GGGTTCTGTG ATG ATTCTTGGCG |
| 13869_putE_A152M-R (SEQ ID NO: 62) | CGCCAAGAAT CAT CACAGAACCC |

Each of the PCR products obtained above was subjected to fusion cloning into the pDZ vector treated with XbaI. The fusion cloning was performed using the In-Fusion® HD Cloning Kit (Clontech Laboratories, Inc.), and the thus-obtained plasmids were named pDZ-NCgl2522_M2, pDZ-NCgl2522_M11, pDZ-NCgl2522_M12, pDZ-NCgl2522_M13, pDZ-NCgl2522_M14, pDZ-NCgl2522_M15, pDZ-NCgl2522_M16, pDZ-NCgl2522_M17, and pDZ-NCgl2522_M18, respectively.

Each of the plasmids prepared above was introduced into DAB12-b via electroporation to obtain transformants, and the thus-obtained transformants were plated on BHIS plate media (37 g/L of Braine heart infusion, 91 g/L of sorbitol, and 2% agar) containing kanamycin (25 µg/mL) and X-gal (5-bromo-4-chloro-3-indolin-D-galactoside) and cultured to form colonies. Among the thus-formed colonies, the strains introduced with the above plasmids were selected.

Each of the strains selected above was cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from $10^{-4}$ to $10^{-10}$, plated on solid media containing X-gal, and cultured to form colonies. Among the thus-formed colonies, white colonies which appeared at a relatively low rate were selected, thereby finally selecting the strains, in which the NCgl2522 gene was substituted each of the variants by a secondary crossover. The finally selected strains were subjected to PCR using a primer pair of SEQ ID NOS: 25 and 26, and the thus-obtained products were applied to sequencing to confirm the substitution with the variants. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named DAB12-b NCgl2522_M2, DAB12-b NCgl2522_M11, DAB12-b NCgl2522_M12, DAB12-b NCgl2522_M13, DAB12-b NCgl2522_M14, DAB12-b NCgl2522_M15, DAB12-b NCgl2522_M16, DAB12-b NCgl2522_M17, and DAB12-b NCgl2522_M18, respectively.

<4-3> Evaluation of Putrescine-Producing Ability of Strains Introduced with NCgl2522 Variants In order to confirm the effect of NCgl2522 variants on putrescine production when the variants of NCgl2522 gene, which increases the ability to export putrescine, was introduced into the putrescine-producing strains, the putrescine-producing ability was compared among the modified strains of *Corynebacterium glutamicum* prepared in Examples 4-1 and 4-2.

Specifically, the modified strains of *Corynebacterium glutamicum* (KCCM11240P NCgl2522_M1; KCCM11240P NCgl2522_M3; KCCM11240P NCgl2522_M4; KCCM11240P NCgl2522_M5; KCCM11240P NCgl2522_M6; KCCM11240P NCgl2522_M7; KCCM11240P NCgl2522_M8; KCCM11240P NCgl2522_M9; KCCM11240P NCgl2522_M10; DAB12-b NCgl2522_M2; DAB12-b NCgl2522_M11; DAB12-b NCgl2522_M12; DAB12-b NCgl2522_M13; DAB12-b NCgl2522_M14; DAB12-b NCgl2522_M15; DAB12-b NCgl2522_M116; DAB12-b NCgl2522_M17; and DAB12-b NCgl2522_M18) and two kinds of parent strains (KCCM11240P and DAB12-b) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, and 2% agar at pH 6.8, based on 1 L), and cultured at 30° C. for 24 hours. About one platinum loop of each strain cultured therefrom was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, 100 µg of biotin, 3 mg of thiamine HCl, 3 mg of calcium-pantothenic acid, 3 mg of nicotinamide, and 5% $CaCO_3$, based on 1 L), and cultured with shaking at 30° C. at a rate of 200 rpm for 50 hours. During culturing of all strains, 1 mM arginine was added to the media. After completion of the culture, the concentration of putrescine produced in each culture was measured, and the results are shown in Table 7 below.

TABLE 7

| Name of Strains | Putrescine (g/L) | Productivity (g/L/h) | Fold (%) |
|---|---|---|---|
| KCCM11240P | 5.8 | 0.116 | 100 |
| KCCM11240P Ncgl2522_M1 | 6.6 | 0.132 | 114 |
| KCCM11240P Ncgl2522_M3 | 6.2 | 0.124 | 107 |
| KCCM11240P Ncgl2522_M4 | 6.2 | 0.124 | 107 |
| KCCM11240P Ncgl2522_M5 | 6.3 | 0.126 | 109 |
| KCCM11240P Ncgl2522_M6 | 6.6 | 0.132 | 114 |
| KCCM11240P Ncgl2522_M7 | 6.6 | 0.132 | 114 |
| KCCM11240P Ncgl2522_M8 | 6.2 | 0.124 | 107 |

TABLE 7-continued

| Name of Strains | Putrescine (g/L) | Productivity (g/L/h) | Fold (%) |
|---|---|---|---|
| KCCM11240P Ncgl2522_M9 | 6.2 | 0.124 | 107 |
| KCCM11240P Ncgl2522_M10 | 6.3 | 0.126 | 109 |
| DAB12-b | 6.5 | 0.129 | 100 |
| DAB12-b Ncgl2522_M2 | 7.2 | 0.144 | 112 |
| DAB12-b Ncgl2522_M11 | 6.8 | 0.136 | 105 |
| DAB12-b Ncgl2522_M12 | 6.8 | 0.136 | 105 |
| DAB12-b Ncgl2522_M13 | 7.0 | 0.140 | 109 |
| DAB12-b Ncgl2522_M14 | 7.2 | 0.144 | 112 |
| DAB12-b Ncgl2522_M15 | 7.2 | 0.144 | 112 |
| DAB12-b Ncgl2522_M16 | 7.0 | 0.140 | 109 |
| DAB12-b Ncgl2522_M17 | 6.9 | 0.138 | 107 |
| DAB12-b Ncgl2522_M18 | 7.0 | 0.140 | 109 |

As shown in Table 7 above, when each of the variants was introduced into KCCM11240P, all of the nine modified strains of *Corynebacterium glutamicum* showed an increase in the putrescine production and productivity compared to the parent strains by 7% to 14%. Additionally, when each of the variants was introduced into DAB12-b, all of the nine modified strains of *Corynebacterium glutamicum* showed an increase in the putrescine production and productivity compared to the parent strains by 5% to 12%. In particular, the productivity represents the putrescine production per hour for each transformant, and was expressed in g/L/h.

EXAMPLE 5

Introduction of NCgl2522 Variants into Putrescine-Producing Strains with Improved Ability to Export Putrescine and Confirmation of Putrescine-Producing Ability Thereof <5-1> Construction of Strains by Introducing NCgl2522 Variants into Strains with Improved Ability to Export Putrescine In order to so confirm the effect of the variants of NCgl2522 gene, NCgl2522_M1, NCgl2522_M3, NCgl2522_M4, NCgl2522_M5, NCgl2522_M6, NCgl2522_M7, NCgl2522_M8, NCgl2522_M9, and NCgl2522_M10 were respectively introduced into the chromosome of KCCM11240P P(CJ7)-NCgl2522 (Korean Patent Application Publication No. 2014-0115244), which is a *Corynebacterium glutamicum* ATCC13032-based putrescine-producing strain with an increased ability to export putrescine.

Specifically, each of the the plasmids pDZ-NCgl2522_M1, pDZ-NCgl2522_M3, pDZ-NCgl2522_M4, pDZ-NCgl2522_M5, pDZ-NCgl2522_M6, pDZ-NCgl2522_M7, pDZ-NCgl2522_M8, pDZ-NCgl2522_M9, pDZ-NCgl2522_M10 prepared in Example 4-1 was transformed into KCCM11240P P(CJ7)-NCgl2522 in the same manner as in Example 4-1, and thus it was confirmed that the NCgl2522 gene was substituted with the variants within the chromosome thereof. The selected modified strains of *Corynebacterium glutamicum* were named KCCM11240P P(CJ7)-NCgl2522 NCgl2522_M1, KCCM11240P P(CJ7)-NCgl2522 NCgl2522_M3, KCCM11240P P(CJ7)-NCgl2522 NCgl2522_M4, KCCM11240P P(CJ7)-NCgl2522 NCgl2522_M5, KCCM11240P P(CJ7)-NCgl2522 NCgl2522_M6, KCCM11240P P(CJ7)-NCgl2522 NCgl2522_M7, KCCM11240P P(CJ7)-NCgl2522 NCgl2522_M8, KCCM11240P P(CJ7)-NCgl2522 NCgl2522_M9, and KCCM11240P P(CJ7)-NCgl2522 NCgl2522_M10, respectively.

<5-2> Evaluation of Putrescine-Producing Ability of Strains Prepared by Introducing NCgl2522 Variants into Strain with Improved Ability to Export Putrescine In order to confirm the effect of NCgl2522 variants on the *Corynebacterium glutamicum* producing strains with an improved ability to export putrescine, the putrescine-producing ability was compared among the modified strains of *Corynebacterium glutamicum* prepared in Example 5-1 and the parent strain.

Specifically, the modified strains of *Corynebacterium glutamicum* (KCCM11240P P(CJ7)-NCgl2522 NCgl2522_M1, KCCM11240P P(CJ7)-NCgl2522 NCgl2522_M3, KCCM11240P P(CJ7)-NCgl2522 NCgl2522_M4, KCCM11240P P(CJ7)-NCgl2522 NCgl2522_M5, KCCM11240P P(CJ7)-NCgl2522 NCgl2522_M6, KCCM11240P P(CJ7)-NCgl2522 NCgl2522_M7, KCCM11240P P(CJ7)-NCgl2522 NCgl2522_M8, KCCM11240P P(CJ7)-NCgl2522 NCgl2522_M9, and KCCM11240P P(CJ7)-NCgl2522 NCgl2522_M10) and the parent strain (KCCM11240P P(CJ7)-NCgl2522) were respectively plated on 1 mM arginine-containing CM plate media (1% glucose, 1% polypeptone, 0.5% yeast extract, 0.5% beef extract, 0.25% NaCl, 0.2% urea, 100 µL of 50% NaOH, and 2% agar at pH 6.8, based on 1 L), and cultured at 30° C. for 24 hours. About one platinum loop of each strain cultured therefrom was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, 100 µg of biotin, 3 mg of thiamine HCl, 3 mg of calcium-pantothenic acid, 3 mg of nicotinamide, and 5% $CaCO_3$, based on 1 L), and cultured with shaking at 30° C. at a rate of 200 rpm for 50 hours. During culturing of all strains, 1 mM arginine was added to the media. After completion of the culture, the concentration of putrescine produced in each culture was measured, and the results are shown in Table 8 below.

TABLE 8

| Name of Strains | Putrescine (g/L) | Productivity (g/L/h) | Fold (%) |
|---|---|---|---|
| KCCM11240P P(CJ7)-Ncgl2522 | 6.9 | 0.138 | 100 |
| KCCM11240P P(CJ7)-Ncgl2522 Ncgl2522_M1 | 7.5 | 0.150 | 109 |
| KCCM11240P P(CJ7)-Ncgl2522 Ncgl2522_M3 | 7.2 | 0.144 | 104 |
| KCCM11240P P(CJ7)-Ncgl2522 Ncgl2522_M4 | 7.2 | 0.144 | 104 |
| KCCM11240P P(CJ7)-Ncgl2522 Ncgl2522_M5 | 7.3 | 0.146 | 106 |
| KCCM11240P P(CJ7)-Ncgl2522 Ncgl2522_M6 | 7.5 | 0.150 | 109 |
| KCCM11240P P(CJ7)-Ncgl2522 Ncgl2522_M7 | 7.6 | 0.152 | 110 |
| KCCM11240P P(CJ7)-Ncgl2522 Ncgl2522_M8 | 7.4 | 0.148 | 108 |
| KCCM11240P P(CJ7)-Ncgl2522 Ncgl2522_M9 | 7.3 | 0.146 | 106 |
| KCCM11240P P(CJ7)-Ncgl2522 Ncgl2522_M10 | 7.3 | 0.146 | 106 |

As shown in Table 8 above, when the nine variants were respectively introduced into KCCM11240P P(CJ7)-NCgl2522 with an improved ability to export putrescine, the modified strains of *Corynebacterium glutamicum* showed an increase in the putrescine production and productivity by 4% to 10% compared to the parent strain, which already showed an improved ability to export putrescine. In particular, the productivity represents the putrescine production per hour for each transformant, and was expressed in g/L/h.

EXAMPLE 6

Construction of NCgl2522 Variant Strains and Confirmation of Arginine-Producing Ability Thereof <6-1> Construction of NCgl2522 Variant Strains from L-Arginine-Producing Strains In order to increase the ability to export L-arginine of the L-arginine-producing strain, NCgl2522_M1, NCgl2522_M3, NCgl2522_M4, NCgl2522_M5, NCgl2522_M6, NCgl2522_M7, NCgl2522_M8, NCgl2522_M9 and NCgl2522_M10, which are variants of NCgl2522 gene, were respectively introduced into the chromosome of *Corynebacterium glutamicum* KCCM10741P (Korean Patent No. 10-0791659).

Specifically, PCR was performed using primer pairs shown in Table 5 based on the genomic DNA of *Corynebacterium glutamicum* KCCM10741P as a template, in the same manner as in Example 4-2, and the strains, in which the NCgl2522 gene was substituted with NCgl2522_M1, NCgl2522_M3, NCgl2522_M4, NCgl2522_M5, NCgl2522_M6, NCgl2522_M7, NCgl2522_M8, NCgl2522_M9 or NCgl2522_M10, were finally selected.

The modified strains of *Corynebacterium glutamicum* selected therefrom were named KCCM10741P NCgl2522_M1, KCCM10741P NCgl2522_M3, KCCM10741P NCgl2522_M4, KCCM10741P NCgl2522_M5, KCCM10741P NCgl2522_M6, KCCM10741P NCgl2522_M7, KCCM10741P NCgl2522_M8, KCCM10741P NCgl2522_M9 and KCCM10741P NCgl2522_M10, respectively.

<6-2> Construction of NCgl2522 Variant Strains from ATCC21831-Based L-Arginine-Producing Strains In order to increase the ability to export L-arginine of the wild-type *Corynebacterium glutamicum* ATCC21831-based L-arginine-producing strain, NCgl2522_M2, NCgl2522_M11, NCgl2522_M12, NCgl2522_M13, NCgl2522_M14, NCgl2522_M15, NCgl2522_M16, NCgl2522_M17 and NCgl2522_M18, which are variants of NCgl2522 gene, were respectively introduced into the chromosome of ATCC21831.

Specifically, PCR was performed using primer pairs shown in Table 5 based on the genomic DNA of *Corynebacterium glutamicum* ATCC21831 as a template, in the same manner as in Example 4-2, and the strains, in which the NCgl2522 gene was substituted with NCgl2522_M2, NCgl2522_M11, NCgl2522_M12, NCgl2522_M13, NCgl2522_M14, NCgl2522_M15, NCgl2522_M16, NCgl2522_M17 and NCgl2522_M18, were finally selected.

The modified strains of *Corynebacterium glutamicum* selected therefrom were named ATCC21831 NCgl2522_M2, ATCC21831 NCgl2522_M11, ATCC21831 NCgl2522_M12, ATCC21831 NCgl2522_M13, ATCC21831 NCgl2522_M14, ATCC21831 NCgl2522_M15, ATCC21831 NCgl2522_M16, ATCC21831 NCgl2522_M17, and ATCC21831 NCgl2522_M18, respectively.

<6-3> Evaluation of L-Arginine-Producing Ability of Strains Introduced with NCgl2522 Variants In order to confirm the effect of NCgl2522 variants on L-arginine production when the variants of NCgl2522 gene, which increases the ability to export L-arginine, into the L-arginine-producing strains, the L-arginine-producing ability was compared among the modified strains of *Corynebacterium glutamicum* prepared in Examples 6-1 and 6-2.

In particular, as the control groups, the *Corynebacterium glutamicum* KCCM10741P and ATCC21831, which are the parent strains, and KCCM10741P_Pcj7 Ncgl2522 and ATCC21831_Pcj7 Ncgl2522, which were prepared in Example 1, were used. One platinum loop of each strain was inoculated into a 250-mL corner-baffled flask containing 25 mL of production media [6% glucose, 3% ammonium sulfate, 0.1% monopotassium phosphate, 0.2% magnesium sulfate heptahydrate, 1.5% corn steep liquor (CSL), 1% NaCl, 0.5% yeast extract, and 100 μg/L of biotin at pH7.2] and cultured with shaking at 30° C. at a rate of 200 rpm for 48 hours to produce L-arginine. After completion of the culture, the L-arginine production was measured by HPLC. The results are shown in Table 9 below.

TABLE 9

| Strains | OD | Arginine Concentration (g/L) | Ornithine Concentration (g/L) | Arginine Fold (%) |
|---|---|---|---|---|
| KCCM10741P | 91 | 3.0 | 0.3 | 100 |
| KCCM10741P_Pcj7 Ncgl2522 | 72 | 3.6 | 0.4 | 120 |
| KCCM10741P_Pcj7 Ncgl2522_M1 | 69 | 4.1 | 0.5 | 136.7 |
| KCCM10741P_Pcj7 Ncgl2522_M3 | 70 | 4.0 | 0.5 | 133.3 |
| KCCM10741P_Pcj7 Ncgl2522_M4 | 70 | 4.0 | 0.5 | 133.3 |
| KCCM10741P_Pcj7 Ncgl2522_M5 | 71 | 3.9 | 0.5 | 130 |
| KCCM10741P_Pcj7 Ncgl2522_M6 | 69 | 4.1 | 0.5 | 136.7 |
| KCCM10741P_Pcj7 Ncgl2522_M7 | 69 | 4.2 | 0.5 | 140 |
| KCCM10741P_Pcj7 Ncgl2522_M8 | 70 | 4.1 | 0.5 | 136.7 |
| KCCM10741P_Pcj7 Ncgl2522_M9 | 70 | 4.0 | 0.4 | 133.3 |
| KCCM10741P_Pcj7 Ncgl2522_M10 | 71 | 4.0 | 0.5 | 133.3 |
| ATCC21831 | 102 | 4.2 | 0.3 | 100 |
| ATCC21831_Pcj7 Ncgl2522 | 86 | 4.8 | 0.4 | 114 |
| ATCC21831_Pcj7 Ncgl2522_M2 | 85 | 5.2 | 0.5 | 123.8 |
| ATCC21831_Pcj7 Ncgl2522_M11 | 85 | 5.1 | 0.5 | 121.4 |
| ATCC21831_Pcj7 Ncgl2522_M12 | 83 | 5.1 | 0.5 | 121.4 |
| ATCC21831_Pcj7 Ncgl2522_M13 | 84 | 5.2 | 0.5 | 123.8 |
| ATCC21831_Pcj7 Ncgl2522_M14 | 84 | 5.2 | 0.5 | 123.8 |
| ATCC21831_Pcj7 Ncgl2522_M15 | 85 | 5.3 | 0.5 | 126.2 |
| ATCC21831_Pcj7 Ncgl2522_M16 | 86 | 5.0 | 0.4 | 119 |
| ATCC21831_Pcj7 Ncgl2522_M17 | 85 | 5.1 | 0.5 | 121.4 |
| ATCC21831_Pcj7 Ncgl2522_M18 | 84 | 5.1 | 0.5 | 121.4 |

As shown in Table 9, when each variant was introduced into KCCM10741P, all of the modified strains of *Corynebacterium glutamicum* introduced with the variants showed an increase in the L-arginine production by 30% and 40% as compared to the parent strains. Additionally, when each variant was introduced into ATCC21831, all of the nine modified strains of *Corynebacterium glutamicum* showed an increase in the L-arginine production by 19% and 26% as compared to the parent strains Further, it was confirmed that the concentration of L-ornithine, which was exported after conversion into L-arginine, also increased when the variants were introduced. Based on these findings, it can be interpreted that the modified strains of *Corynebacterium glutamicum* may also export products biosynthesized from ornithine as a starting material.

In conclusion, the present inventors have confirmed that the amino acid residue at position 152 from the N-terminus plays a key role in the ability to export ornithine-based products in NCgl2522, a putrescine-exporting protein. In particular, when the amino acid at position 152 was substituted with other amino acid residues, it was found that the production of the ornithine-based products was increased in the strains introduced with the variants. Accordingly, the variants of the present disclosure can be applied to a method for producing ornithine-based products using microorganisms to further improve the production thereof, and thus can be very useful for the production of ornithine-based products using biomass.

In the present disclosure, NCgl2522_A152S, a variant of NCgl2522 gene, was introduced into the chromosome of the *Corynebacterium glutamicum* ATCC13032-based putrescine-producing strain, and as a result, it was confirmed that putrescine could be produced with high yield and high productivity in the *Corynebacterium glutamicum* strain introduced with the variant. Accordingly, the strain was named KCCM11240P NCgl2522_A152S and deposited at the Korean Culture Center of Microorganisms (KCCM), an International Depositary Authority, under Budapest Treaty on Sep. 1, 2016 with Accession No. KCCM11887P.

One of ordinary skill in the art will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A polypeptide having putrescine or arginine export activity and comprising an amino acid sequence that has at least 90% sequence identity to the amino acid sequence of SEQ ID NO: 1 or SEQ ID NO: 2, and wherein the alanine at the position corresponding to residue 152 of SEQ ID NO: 1 or SEQ ID NO: 2 is substituted with a different amino acid in the amino acid sequence of the polypeptide.

2. The polypeptide of claim 1, wherein the alanine at the position corresponding to residue 152 of SEQ ID NO: 1 or SEQ ID NO: 2 is substituted with serine, asparagine, histidine, proline, lysine, glutamic acid, cysteine, glutamine, or methionine.

3. The polypeptide of claim 1, wherein the polypeptide consists of the amino acid sequence of any one of SEQ ID NO: 3 to SEQ ID NO: 20.

4. A polynucleotide comprising a nucleotide sequence encoding the polypeptide of claim 1.

5. A vector comprising the polynucleotide of claim 4.

6. A microorganism of the genus *Corynebacterium*, wherein the microorganism produces putrescine and comprises the polypeptide of claim 1.

7. The microorganism of claim 6, wherein the microorganism is *Corynebacterium glutamicum*.

8. The microorganism of claim 6, wherein the microorganism further comprises an ornithine decarboxylase (ODC).

9. The microorganism of claim 6, wherein a gene encoding at least one polypeptide selected from the group consisting of ornithine carbamoyltransferase and a protein involved in glutamate export is inactivated.

10. The microorganism of claim 6, wherein expression of a polynucleotide encoding at least one polypeptide selected from the group consisting of acetyl gamma glutamyl phosphate reductase (ArgC), acetylglutamate synthase or ornithine acetyltransferase (argJ), acetylglutamate kinase (ArgB), and acetylornithine aminotransferase (ArgD) is enhanced compared to a corresponding wild-type microorganism of the genus *Corynebacteriumthc*.

11. The microorganism of claim 6, wherein a gene encoding putrescine acetyltransferase is inactivated.

12. A microorganism of the genus *Corynebacterium*, wherein the microorganism produces arginine and comprises the polypeptide of claim 1, and wherein the arginine-producing ability of the microorganism is enhanced compared to a corresponding microorganism of the genus *Corynebacterium* that does not comprise the polypeptide of claim 1.

13. The microorganism of claim 12, wherein expression of a polynucleotide encoding at least one polypeptide selected from the group consisting of acetyl gamma glutamyl phosphate reductase (ArgC), acetylglutamate synthase or ornithine acetyltransferase (argJ), acetylglutamate kinase (ArgB), and acetylornithine aminotransferase (ArgD) is enhanced compared to a corresponding wild-type microorganism of the genus *Corynebacterium*.

14. The microorganism of claim 12, wherein expression of a polynucleotide encoding at least one polypeptide selected from the group consisting of ornithine carbamoyltransfrase (ArgF), argininosuccinate synthase (argG), argininosuccinate lyase (argH), aspartate ammonia lyase and aspartate aminotransferase is increased compared to a corresponding wild-type microorganism of the genus *Corynebacterium*.

15. The microorganism of claim 12, wherein the microorganism is *Corynebacterium glutamicum*.

16. A method for producing putrescine, comprising:
(i) culturing the microorganism of claim 6 in a medium; and
(ii) recovering putrescine from the microorganism or the medium.

17. A method for producing arginine, comprising:
(i) culturing the microorganism of claim 12 in a medium; and
(ii) recovering arginine from the microorganism or the medium.

18. A microorganism, wherein the microorganism produces putrescine or arginine and comprises the polypeptide of claim 1.

19. The microorganism of claim 18, wherein expression of a polynucleotide encoding at least one polypeptide selected from the group consisting of acetyl gamma glutamyl phosphate reductase (ArgC), acetylglutamate synthase or ornithine acetyltransferase (argJ), acetylglutamate kinase (ArgB), and acetylornithine aminotransferase (ArgD) is enhanced compared to a corresponding wild-type microorganism of the genus *Corynebacterium*.

20. The microorganism of claim 18, wherein the microorganism is *Corynebacterium glutamicum*.

21. A method for producing putrescine or arginine, comprising:
(i) culturing the microorganism of claim 18 in a medium; and
(ii) recovering putrescine or arginine from the microorganism or the medium.

* * * * *

UNITED STATES PATENT AND TRADEMARK OFFICE
CERTIFICATE OF CORRECTION

PATENT NO. : 10,870,871 B2  
APPLICATION NO. : 16/622087  
DATED : December 22, 2020  
INVENTOR(S) : Seon Hye Kim et al.

Page 1 of 1

It is certified that error appears in the above-identified patent and that said Letters Patent is hereby corrected as shown below:

In the Claims

Column 95, Claim 10, Line 39:
"Corynebacteriumthc." should read: --Corynebacterium.--

Signed and Sealed this
Seventh Day of December, 2021

Drew Hirshfeld
*Performing the Functions and Duties of the
Under Secretary of Commerce for Intellectual Property and
Director of the United States Patent and Trademark Office*